(12) United States Patent
Heidel

(10) Patent No.: US 8,069,061 B2
(45) Date of Patent: Nov. 29, 2011

(54) COMPUTER SOFTWARE PROGRAM FOR MENTAL HEALTH PROFESSIONALS

(75) Inventor: Robert Eric Heidel, Oak Ridge, TN (US)

(73) Assignee: Robert Eric Heidel, Oak Ridge, TN (US)

( * ) Notice: Subject to any disclaimer, the term of this patent is extended or adjusted under 35 U.S.C. 154(b) by 438 days.

(21) Appl. No.: 12/387,989

(22) Filed: May 11, 2009

(65) Prior Publication Data

US 2010/0023349 A1 Jan. 28, 2010

Related U.S. Application Data

(60) Provisional application No. 61/127,322, filed on May 12, 2008.

(51) Int. Cl.
*G06F 19/00* (2006.01)
(52) U.S. Cl. .......................................................... 705/3
(58) Field of Classification Search ........................ 705/3
See application file for complete search history.

(56) References Cited

U.S. PATENT DOCUMENTS

| | | | |
|---|---|---|---|
| 5,961,332 A | 10/1999 | Joao | |
| 6,067,523 A | 5/2000 | Bair | |
| 6,071,236 A | 6/2000 | Iliff | |
| 6,120,440 A | 9/2000 | Goknar | |
| 6,283,761 B1 | 9/2001 | Joao | |
| 7,043,025 B2 | 5/2006 | Alldredge | |
| 7,181,017 B1 | 2/2007 | Nagel et al. | |
| 7,428,494 B2 | 9/2008 | Hasan | |
| 7,440,904 B2 | 10/2008 | Hasan | |
| 7,464,040 B2 | 12/2008 | Joao | |
| 7,475,020 B2 | 1/2009 | Hasan | |
| 7,490,048 B2 | 2/2009 | Joao | |
| 7,509,264 B2 | 3/2009 | Hasan | |
| 7,630,986 B1 | 12/2009 | Herz et al. | |

*Primary Examiner* — Gerald J. O'Connor
*Assistant Examiner* — John Pauls

(57) ABSTRACT

A computer software program that will allow mental health practitioners to enter data into portable files and send information to various professional organizations, institutions, businesses, and/or entities through a direct, secure, and electronic linkage created by registering with said professional organizations, institutions, businesses, and/or entities. Mental health professionals using the software program will be able to create portable files containing information about clients, notes, credentials, licenses, certifications, specializations, accreditations, professional memberships, professional trainings, Continuing Education Units, professional activities, supervision hours, education, insurance board memberships. A plethora of relevant professional mental health information will be accessible through the software program. Professional organizations, institutions, businesses, and/or entities will be able to advertise and/or send information pertaining to products and services. The software program is a "one-stop shopping" platform for mental health professionals to create portable files and send information in a streamlined and efficient manner.

10 Claims, 23 Drawing Sheets

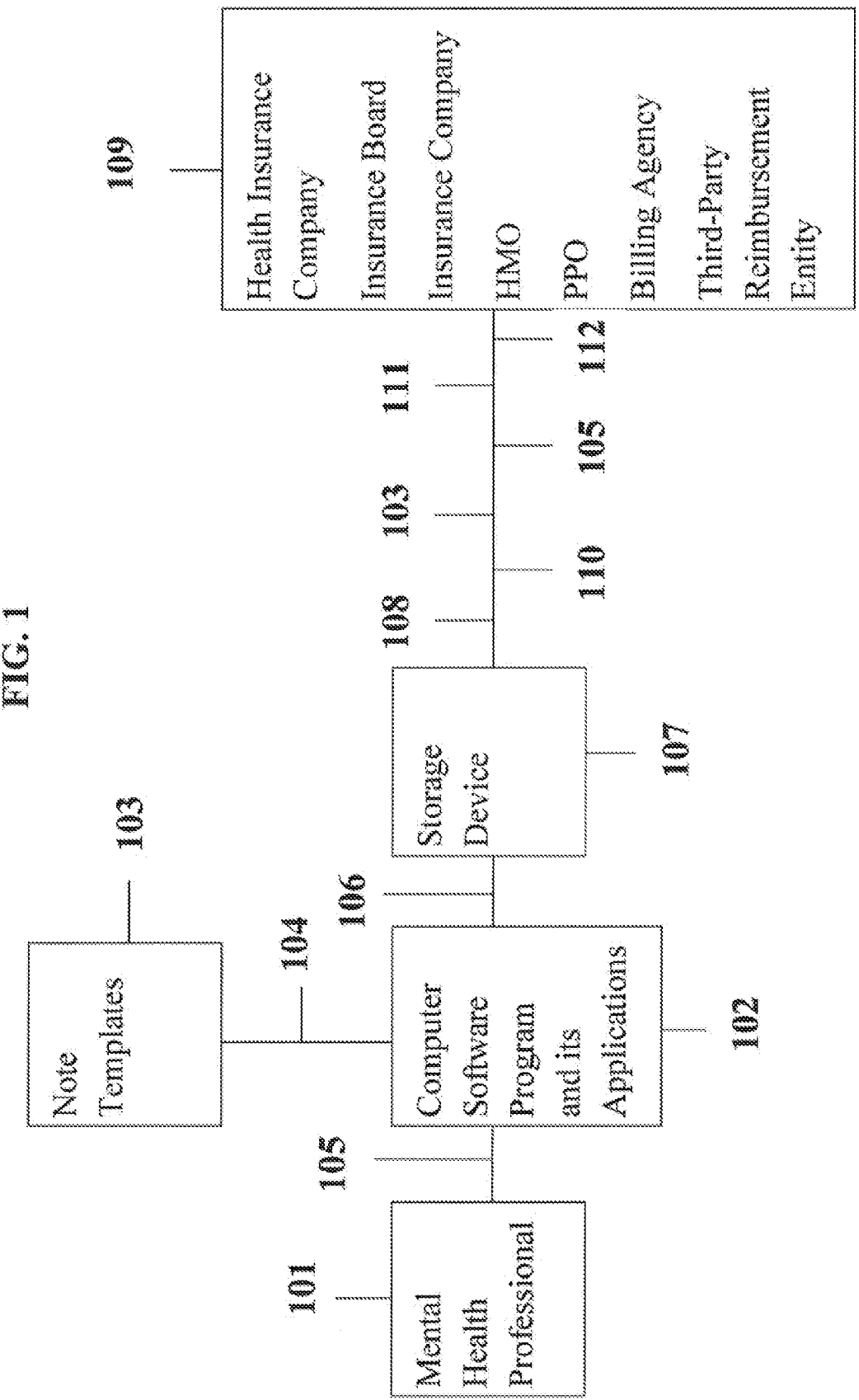

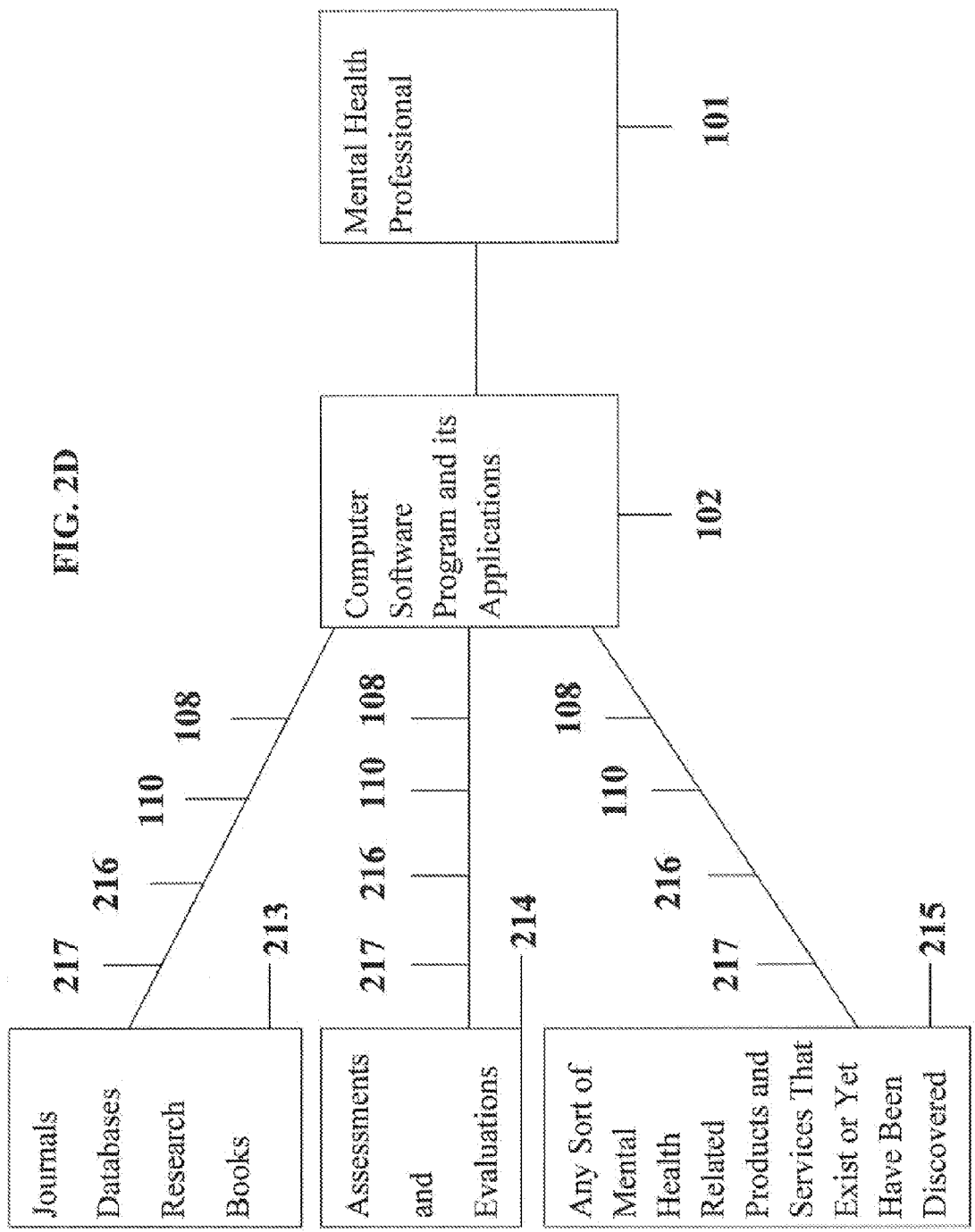

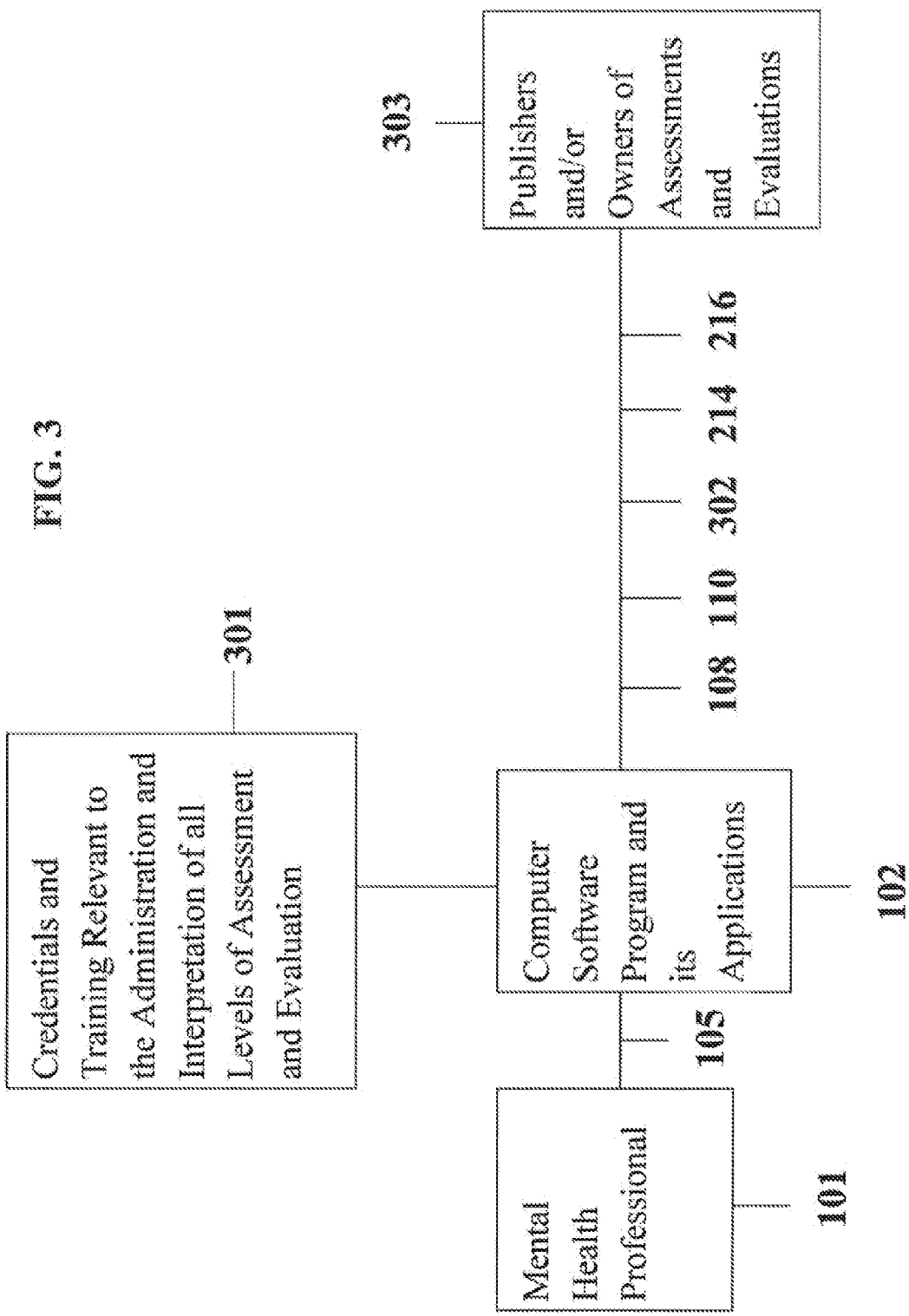

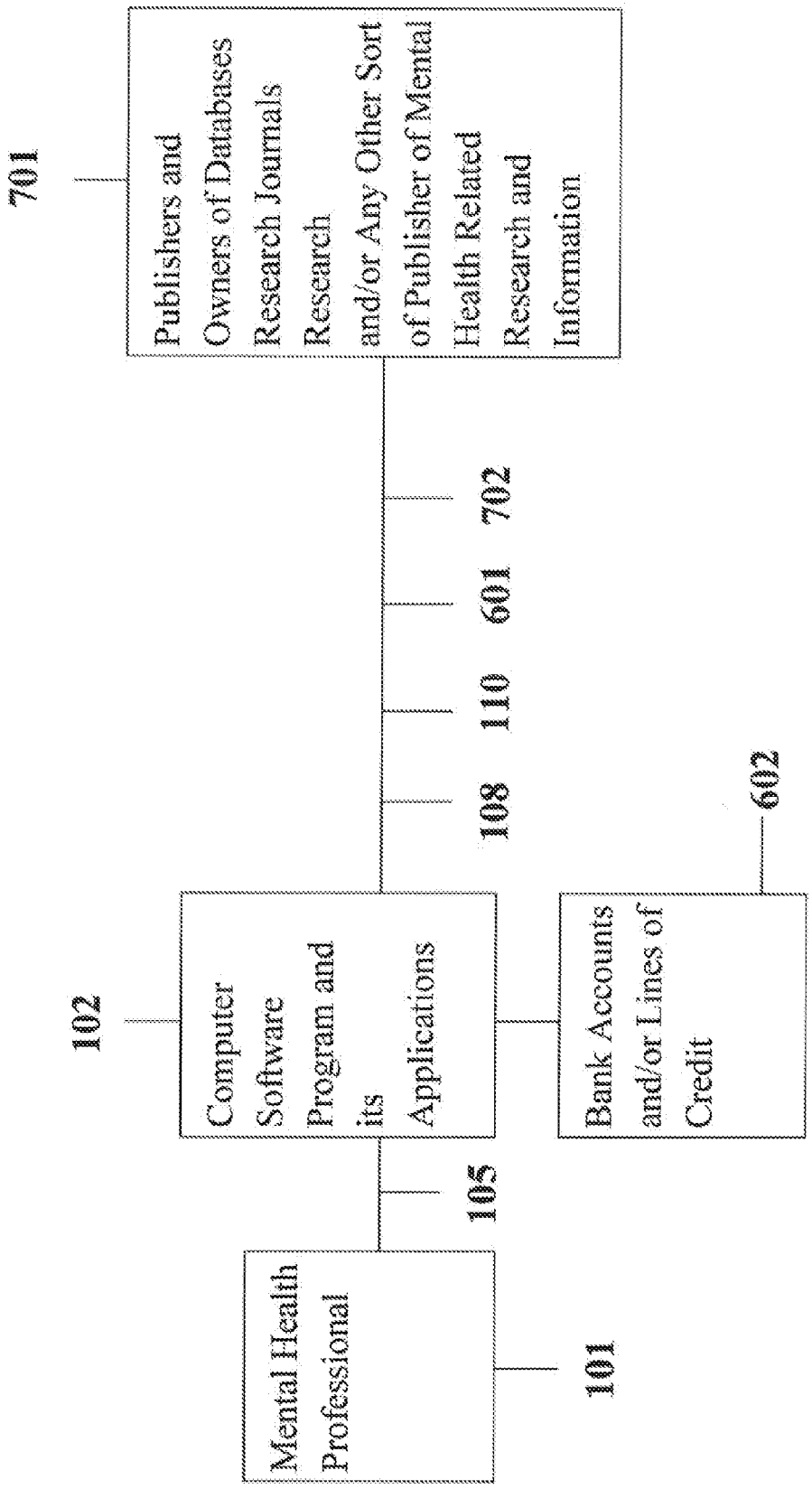

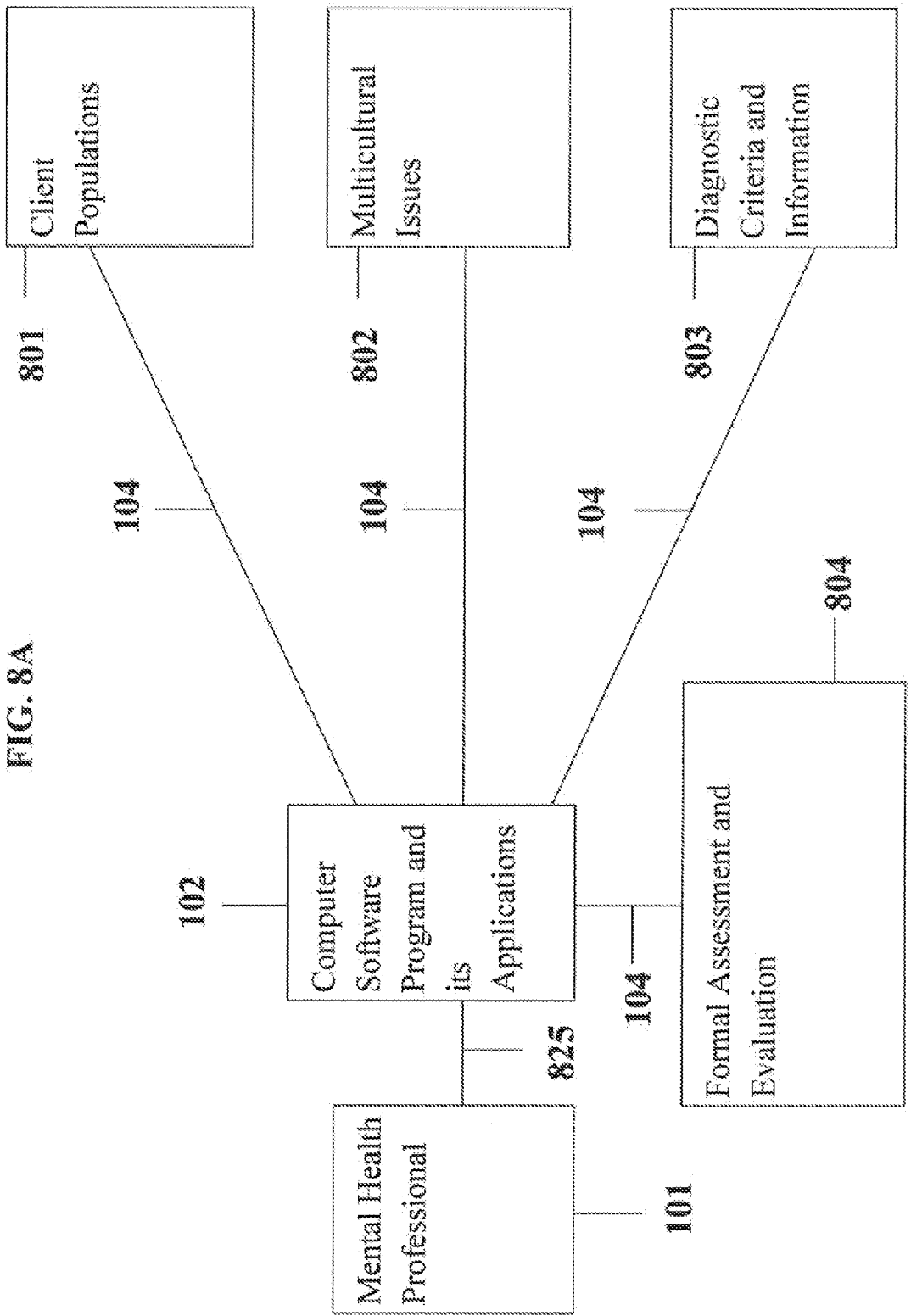

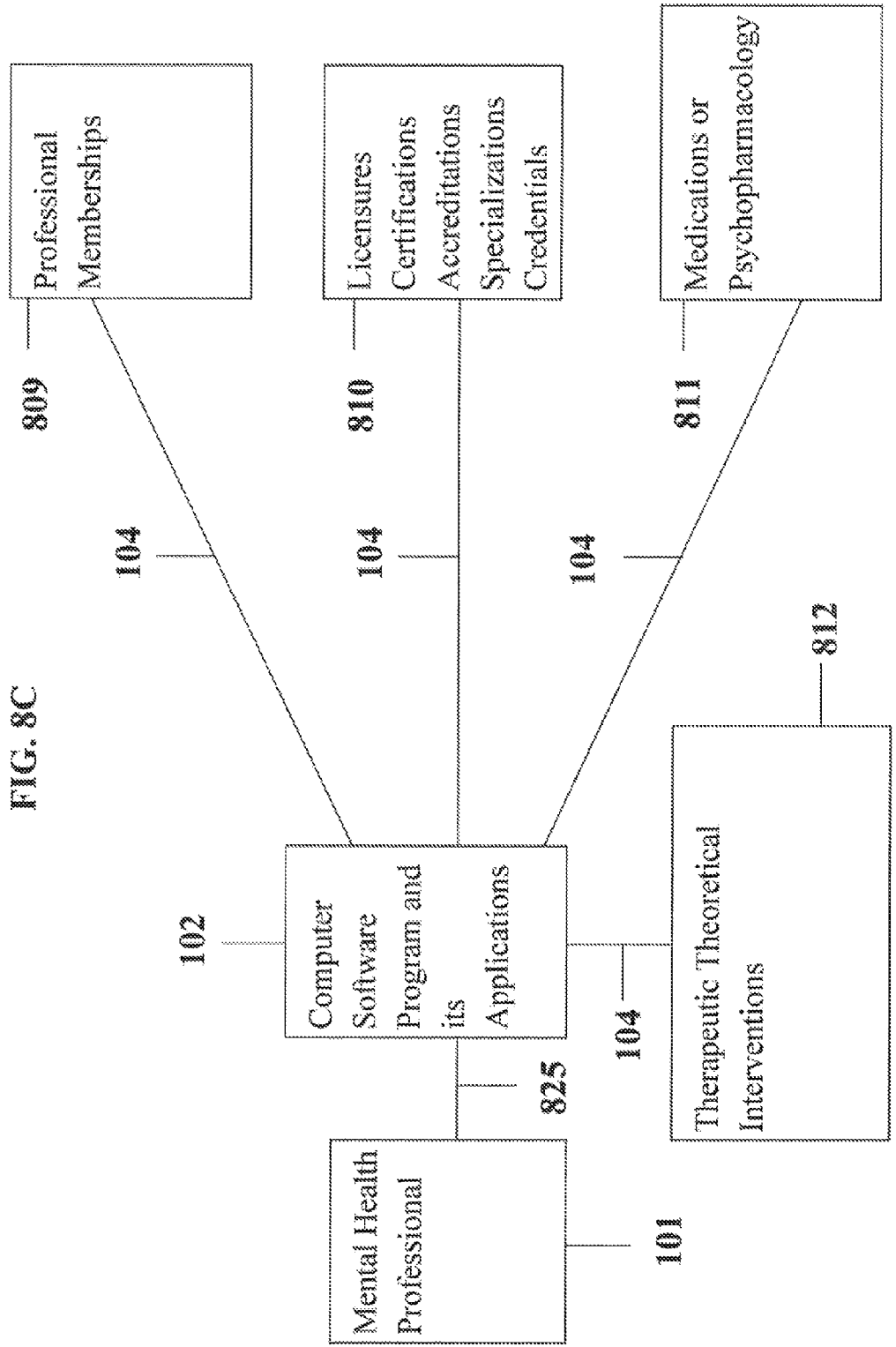

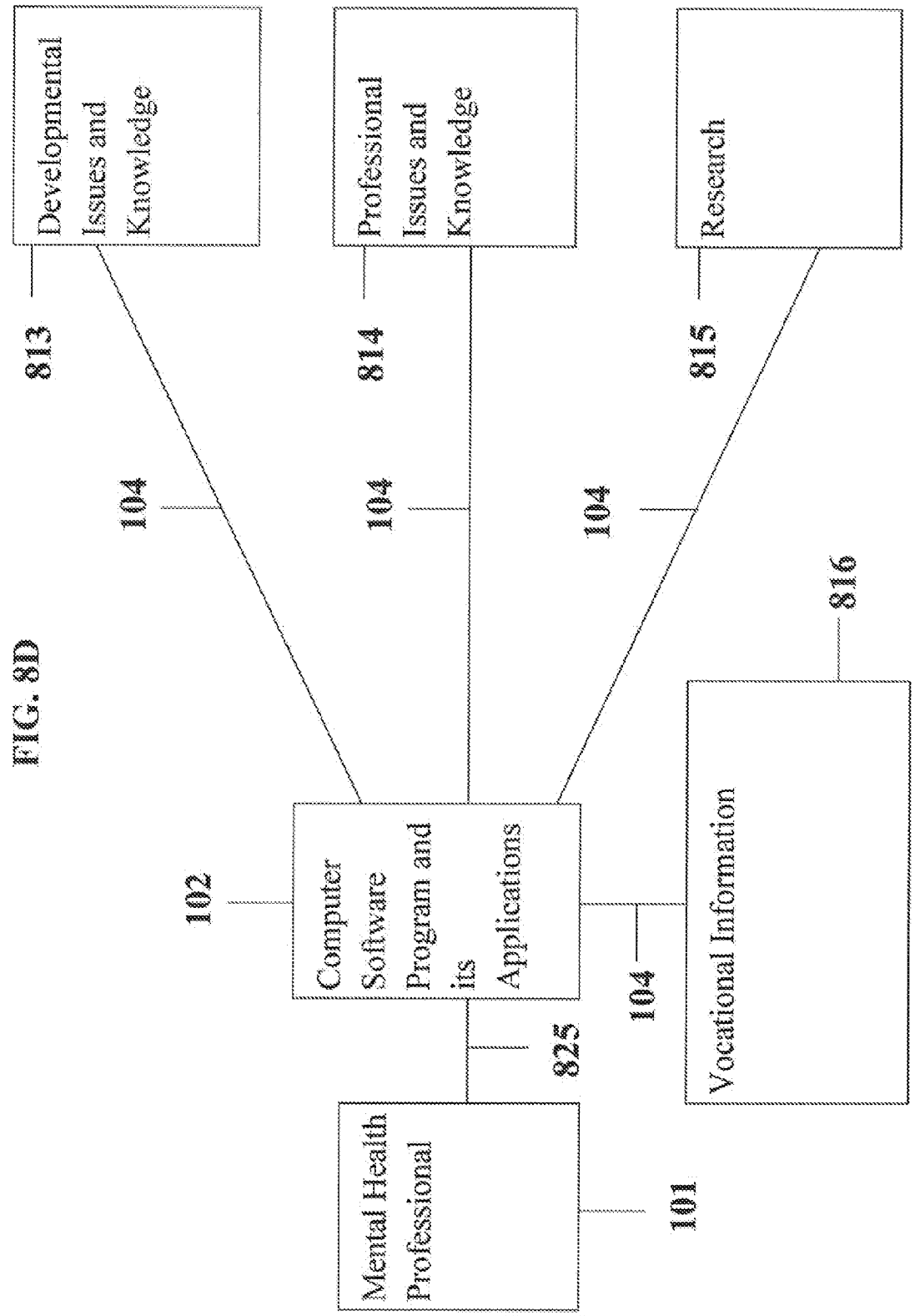

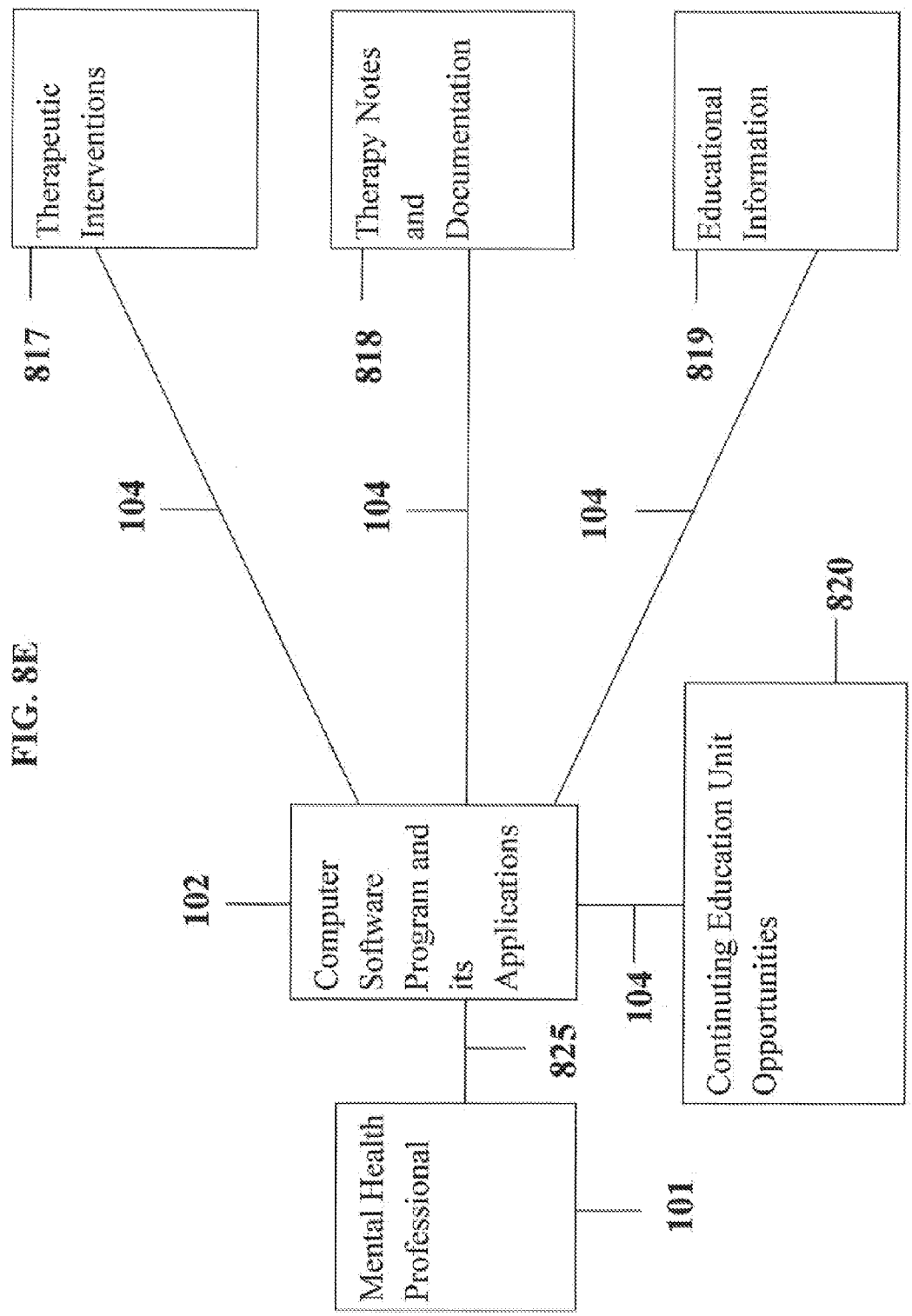

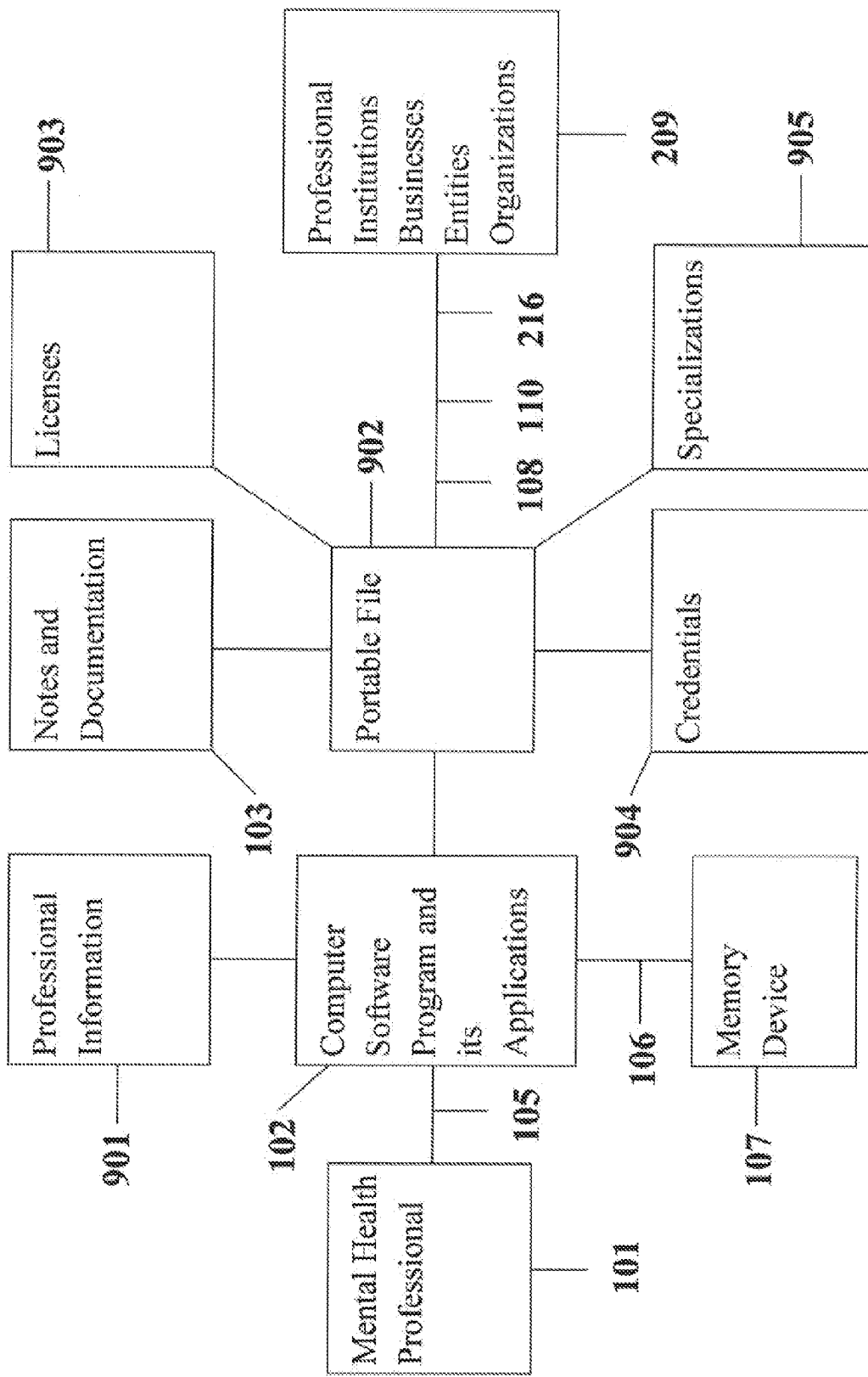

COMPUTER SOFTWARE PROGRAM FOR MENTAL HEALTH PROFESSIONALS

CROSS-REFERENCE TO RELATED APPLICATIONS

U.S. Provisional Application No. 61/127,322, Computer Software Program for Mental Health Professionals

FEDERALLY SPONSORED RESEARCH

Not Applicable

SEQUENCE LISTING

Not Applicable

BACKGROUND OF THE INVENTION

1. Field of Invention

This invention relates to a software program with various applications for mental health professionals, specifically applications related to conducting professional, ethical, legal, academic, and business tasks associated with mental health practice.

2. Discussion of Prior Art

Traditionally, professionals working in mental health related fields have had to put a lot of effort into keeping track of their day to day professional activities, competencies, memberships, and responsibilities. In regards to note-taking and insurance billing, professionals must keep past and current notes on their therapeutic sessions and often times a file of notes printed or written on paper. Professionals then must send their notes to insurance companies and HMOs for reimbursement and often use third-party billing agencies. The process of writing notes and getting reimbursement has been done electronically or by mail in the past. Also, in terms of keeping up and paying for memberships, accreditations, licensures, certifications, insurance boards, CEUs, and trainings, mental health professionals have either had to deal with many different organizations person to person, electronically, via mail, by telephone, or by any number of means. Advertising for various mental health related professional associations, memberships, organizations, products, CEUs, and opportunities also have come from a varying set of communication mediums.

In the past, when a professional wants to give a formal assessment and/or evaluation they had to contact a publisher to receive permission and copies of the assessment and/or evaluation in order to give it. Publishers also had to have a professional's credentials to determine if they were able to give either Level A, Level B, and/or Level C assessments and/or evaluations. Mental health professionals must have proper training and/or education in order to administer and interpret certain types of assessments and evaluations.

In the past, when mental health professionals have needed to access information about multicultural issues, diagnostic criteria, ethical data, legal data, job offerings, CEU opportunities, medications, psychopharmacology, social services, theoretical orientations, interventions, research, and any other sort of relevant mental health related data they had to go to a number of differing sources located in differing areas such as the internet, books, journals, consultants, bodies of knowledge, and so forth.

Professionals in the past also have had to purchase access to different journals and research-based publications through many different outlets and have them delivered by mail or other mediums. Advertising and targeting audiences by mental health-oriented organizations, institutions, and/or businesses has also occurred through a variety of mediums. Professional mental health practitioners also have had to maintain professional activities through a variety of mediums and volitions when it comes to dealing with mental health organizations, businesses, and/or institutions. Mental health professionals have had to conduct their own statistical analyses on their data in a myriad of ways from certain software packages to doing it by hand or having a statistician or accounting professional do it for them when it is needed.

Portability of some forms of professional mental health information has not existed up to this point. Tracking information such as supervision hours, credentials, licenses, accreditations, specializations, professional memberships, time and activities spent meeting the requirements of professional memberships, insurance board membership, Continuing Education Units, and other kinds of information has been tedious in the past due to no portability or uniformity in the tracking of and sending of this kind of information to third parties.

Finally, mental health professionals have paid for many things associated with their professional practice and have had to deal with paying for products and/or services in many manners and through many mediums. The computer software program in this patent disclosure provides a new way for mental health professionals to facilitate their professional duties, responsibilities, and/or work in a myriad of new ways that expedites the ability for mental health professionals to facilitate said duties, responsibilities and work in a more efficient, secure, and electronic manner.

OBJECTS AND ADVANTAGES

Accordingly, this software program with applications has many advantages over past programs and applications and they are:

(a) Portability of relevant professional mental health information such as CEUs, supervision hours, professional memberships, credentials, licenses, specializations, certifications, accreditations, trainings, insurance information, notes, professional activities, hours, information, assessments and evaluations, credit and/or monetary information, vitae, and information pertaining to professional ethical, and legal duties of mental health professionals (b) The creation of direct, secure, and electronic linkages between the software program and various professional mental health entities, insurance companies, local, state, and federal institutions, and businesses for electronic transmission of pertinent data in a timely and secure fashion (c) The software program and applications allow for mental health professionals to access information on a plethora of different topics related to mental health practice (d) Allows for businesses and entities to advertise directly to their consumer demographics and markets (e) Allows for mental health professionals to create a linkage to all of the professional organizations they have membership with so that information can be exchanged between the two in a streamlined and timely fashion (f) The software program can be used by all different kinds of mental health professionals (g) The software program will allow for mental health professionals to conduct statistical analyses on professional duties and responsibilities (h) Allows mental health professionals to conduct safe credit and monetary transactions with various entities (i) Allows for mental health professionals to register with various entities so that information can be exchanged in a timely fashion through a direct, secure, and electronic linkage between the software and said entities

SUMMARY

This non-provisional application pertains to an embodiment of a computer software program and applications that is a "one-stop shopping" application for counselors, psychologists, school counselors, school psychologists, clinical social workers, clinicians, researchers, psychiatrists, students, professors, and anyone person or object associated with mental health fields and/or psychology. The computer program provides fast and secure access to a number of relevant and relative applications within the fields of therapy, counseling, psychology, assessment and evaluation, diagnosis, multicultural issues, medications, psychopharmacology, insurance companies, insurance boards, professional organizations, certifications, licensures, credentials, accrediting bodies, CEU's, professional journals, ethics, note-taking, contracts, note templates, insurance billing, legal statutes, legal advice, job offerings, current and past research, statistical analyses, university-setting applications, professional-setting applications, medical and psychiatric knowledge, client tracking, business tracking, financial tracking, time tracking, data tracking, databases, database management, telemed, and/or any other sort of undertaking associated with the conducting of therapeutic, psychological, counseling-oriented, psychiatric, medical, business-oriented, professional, clerical, rehabilitative, education-oriented, and/or record keeping functions that exists or has yet been discovered. There is also the potential to advertise and/or provide information about CEU opportunities, conferences, books, journals, medications, universities, events, programs, certifications, licensures, alerts, job openings, trainings, various opportunities, organizations, memberships, products that exist or have yet been discovered, databases, and/or any other kind of advertisement associated with counseling, schools, psychology, medicine, psychiatry, social work, case management, medications, and/or education that exists or yet has been discovered. The computer program will have direct, secure, and electronic linkages and access through existing and/or yet to be discovered electronic, internet, and web-based connections to various professional mental health institutions, entities, businesses, organizations, institutions of higher learning, universities, communication mediums that exist or have yet been discovered, billing agencies, insurance companies, monetary and credit transactions, internet sites and/or businesses, publishers, databases, journals, research, legal statutes, ethics codes, and/or information of any kind that exists or has yet been discovered associated with the conducting of professional activities in the mental health field. This computer program will provide the means for professional efficiency in all realms of therapy, counseling, education, psychology, psychiatry, medicine, business, professional mental health duties, responsibilities, and work and/or any other professional activity associated with professional mental health, medical, and/or psychological fields.

BRIEF DESCRIPTION OF THE DRAWINGS

FIG. 1. This figure depicts mental health professional notes and/or documents being completed using the computer software program using templates and/or designs as well as the direct electronic linkage and delivery of said documents to insurance companies, insurance boards, third-party reimbursement, HMOs, PPOs, health insurance companies, and/or any other sort of business that exists or has yet been discovered.

FIGS. 2A, 2B, 2C, and 2D. These figures depict the ability to send information and advertise about mental health related products and/or services using the computer software program and its applications via direct, secure, and electronic linkages with various mental health related businesses, organizations, and/or institutions. The linkage is created by the computer software program by a mental health professional registering with said businesses, organizations, and/or institutions that exist or have yet been discovered using the computer software program and its applications.

FIG. 3. This figure depicts how formal and informal evaluations and assessments can be accessed, utilized, and purchased from publishers and/or owners of said evaluations and assessments using the computer software program and its applications.

FIG. 7. This figure depicts how a user of the computer software program and its applications can access databases and/or research relevant and related to the mental health field.

FIGS. 8A, 8B, 8C, 8D, 8E, and 8F. These figures depict how a user of the computer software program and its applications can access and utilize various kinds of mental health and professional information.

FIGS. 9A, 9B, 9C, and 9D. These figures depict how a mental health professional can create portable files containing professional information and send it electronically to various professional businesses, organizations, and/or institutions

DRAWINGS

List of Reference Numerals

Figure 2A:
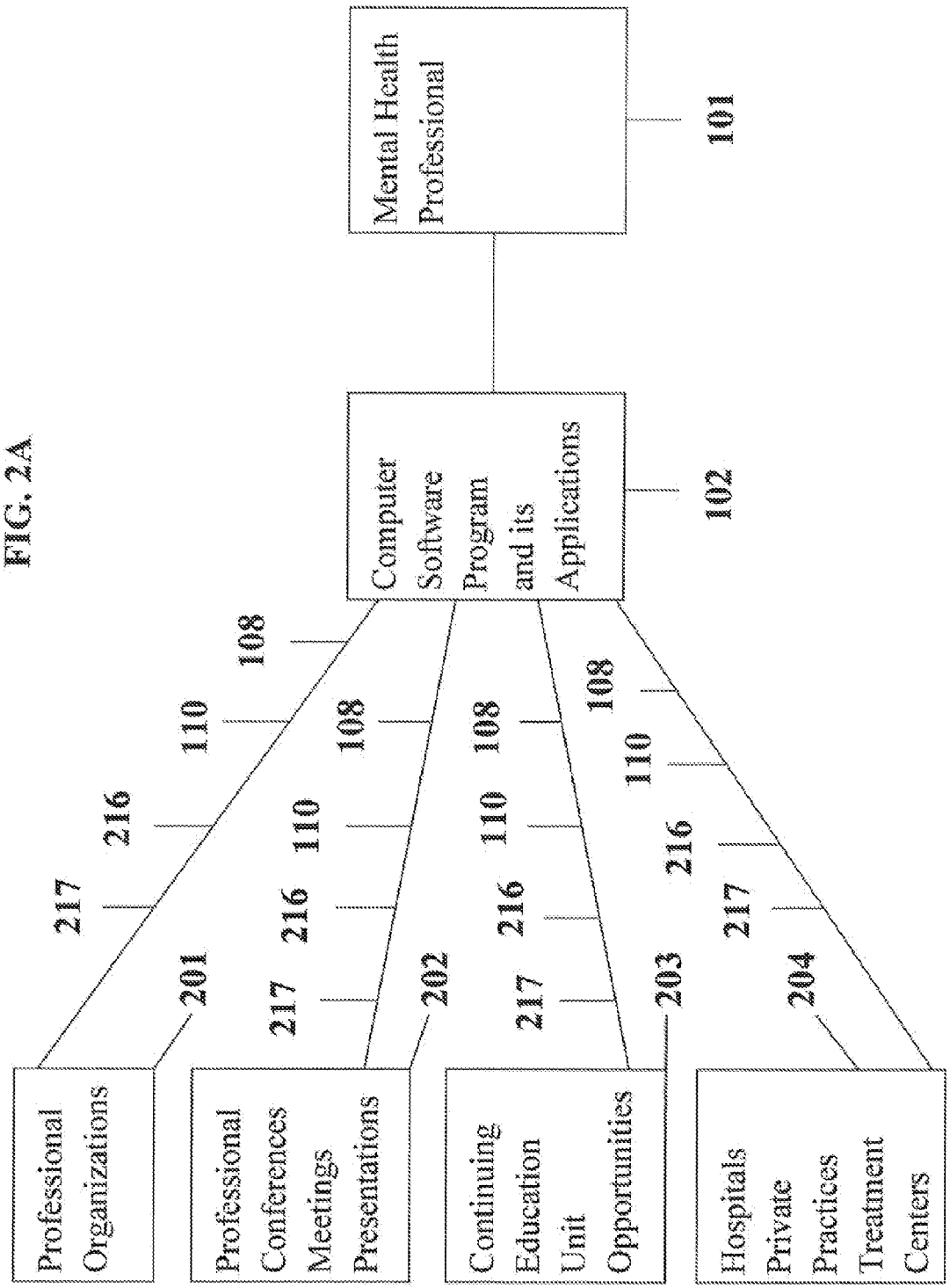

101—Mental Health Professional
102—Computer Software Program and Its Applications
103—Note Templates
104—Preinstalled or Uploaded
105—Data
106—Save
107—Storage Device
108—Register
109—Health Insurance Company, Insurance Board, Insurance Company, HMO, PPO, Billing Agency, Third-Party Reimbursement Company and/or Entity
110—Direct, Secure, and Electronic Linkage
111—Reimbursement
112—Electronic Fund Transfer Solution
201—Mental Health Related Professional Organizations
202—Professional Conferences, Meetings, Presentations
203—Continuing Education Unit (CEU) Opportunities 204—Hospitals, Private Practices, Treatment Centers
205—Job Postings, Universities
206—Professional Trainings, Professional Events, Professional Memberships
207—Credentialing Opportunities, Specialization Opportunities, Licensing Opportunities
208—Publishing Companies, Pharmaceutical Companies
209—Professional Mental Health Related Institutions, Businesses, Entities, and/or Organizations
210—Professional mental Health Related Products and Services
211—Mental Health Related Educational Programs
212—Medications
213—Journals, Databases, Research, Books
214—Assessments and Evaluations
215—Any Mental Health Related Product or Service That Exists or Yet Has Been Discovered
216—Advertise and/or Send Information
217—Pay
301—Credentials and Training Relevant to the Administration and Interpretation of All Levels of Assessment and Evaluation within Professional Mental Health
302—Access, Purchase, and/or Utilize (assessments and evaluations)
303—Publishers and/or Owners (of assessments and evaluations)
401—Hours, Evidence, Duties, Responsibilities, and/or Activities
501—Statistical Analyses
502—Personal Trends in Diagnosis and Treatment
503—Client Population Demographics
504—Business Expenses
505—Tracking of Client Attendance and Issues
506—Business Income
507—Time and Activities Spent Meeting Professional Requirements (statistical analyses)
508—Insurance Reimbursement (statistical analyses)
509—Supervision Hours
510—CEU Hours (statistical analyses)
511—Trainings (statistical analyses)
512—Assessment and Evaluation Practices (statistical analyses)
513—Any Sort of Professional Activity and/or Function Mental Health Professionals Would Have Interest in Tracking (statistical analyses)
601—Facilitate Secure Monetary and Credit Transactions
602—Bank Accounts and/or Lines of Credit
701—Publishers and Owners of Databases, Research Journals, Research, and/or Any Other Sort of Publisher of Mental Health Research and Information
702—Access (of databases, research journals, research, and publications)
801—Client Populations (information)
802—Multicultural Issues (information)
803—Diagnostic Criteria and Information (information)
804—Formal Evaluation and Assessment (information)
805—Statistics (information)
806—Ethics Codes (information)
807—Legal Statutes (information)
808—Professional Organizations, Institutions, Businesses, and/or Entities (information)
809—Professional Memberships (information)
810—Licensures, Certifications, Accreditations, Specializations, and/or Credentials (information)
811—Medications and/or Psychopharmacology (information)
812—Therapeutic Theoretical Orientations (information)
813—Developmental Issues and Knowledge (information)
814—Professional Issues and Knowledge (information)
815—Research (information)
816—Vocational Information (information)
817—Therapeutic Interventions (information)
818—Therapy Notes and Documentation (information)
819—Educational Information (information)
820—Continuing Education Unit Opportunities (information)
821—Consultation (information)
822—Professional Discourse and Communication (information)
823—Supervision Practices and Regulations (information)
824—Any Sort of Information Related to the Professional Practice and Duties of a Mental Health Professional That Exists or Has Yet Been Discovered
825—Purchases the Rights
901—Professional Information
902—Portable File
903—Licenses (portable file)
904—Credentials (portable file)
905—Specializations (portable file)
906—Accreditations (portable file)
907—Education (portable file)
908—CEUs (portable file)
909—Trainings (portable file)
910—Supervision Hours (portable file)
911—Professional Memberships (portable file)
912—Any Other Sort of Professional Information (portable file)

DETAILED DESCRIPTION

This patent disclosure pertains to an embodiment of computer software program that can be used by mental health professionals to complete tasks and applications associated with professional activities, competencies, duties, and responsibilities. The computer software program is a "one-stop shopping" software application for all relevant responsibilities and duties that a mental health professional does on a day-to-day basis and over the course of their career. The computer software program will contain applications that will expedite the processes by which mental health professionals conduct their business and professional duties.

The mental health professional will purchase the rights to use the computer software program and its applications. The mental health professional will then install and/or download the computer software program and its applications to a computer. The computer software program can be written to a disk and/or downloaded electronically and then installed into a computer's hard drive, memory, and/or RAM. The computer's operating system software would then interface with the computer's hardware to execute the applications of the computer software program. The computer software program can be written in any high-level programming language, machine language, and/or assembly language that exists or yet has been discovered and can be compiled, interpreted, and/or assembled into machine language object code by any means that exists or has yet been discovered. The computer software program would be loaded into the computer's storage so that it can be executed. The mental health professional could then interface with the computer software program to facilitate professional duties that can be conducted using the computer software program and its applications by inputting data via various graphical user interfaces and receiving outputs. The instructions contained in the computer software program and its applications would pass from the software itself, through the system software and operating software, to the computer hardware that receives the instruction as the aforementioned machine code. These instructions will make the computer facilitate the operations and applications that this computer software program allows for mental health professionals to carry out. These instructions can be performed sequentially, conditionally, and/or iteratively depending upon the applications of the computer software program that the mental health professional is using. The interconnection between networks (be it LAN, WAN, WLAN, and/or WWAN networks) of the mental health professional using the computer software program and its applications and the various mental health oriented businesses, organizations, entities, and/or institutions can be facilitated using any means that exists or has yet been discovered for business-to-business (B2B), business-to-consumer (B2C), and/or consumer-to-consumer (C2C) communications and transactions. With the many instances within the applications of the computer software program where sensitive information is being exchanged, any form of a communications security mechanism can be used to create the direct, secure, and electronic linkage between networks of the mental health professional and the various businesses, organizations, entities, and/or institutions. Actions and applications of the computer software program will occur between respective servers of the mental health professional and the entities they conduct professional activities with using the computer software program and its applications. The registration and creation of direct, secure, and electronic linkages between mental health professionals using the computer software program and its applications and various professional organizations, businesses, institutions, and/or entities so that information and/or monetary and credit transactions can be exchanged is of paramount importance within this patent disclosure. The data sent via said linkages can be encrypted at any existing or yet to be discovered bit level to ensure security and protection of data. The inputting and saving of relevant professional mental health data through interfacing can be done by any means that exists or has yet been discovered.

The computer software program will have an application associated with the taking of notes necessary for tracking client progress and monetary reimbursement for services rendered. Within the computer software program will be an application that allows for a user to fill in relevant client or professional activity data onto a template that is reliable and valid for the keeping of records. This note template can be of any design or structure that exists or has yet been discovered. The user will fill in data onto the note template using a computer with the computer software program installed. The user will type in the data associated with their client contact and/or professional activity and save it to their computer and/or any other sort of storage device that can save data that exists or has yet been discovered. Another aspect of the application relevant to the taking of client and/or professional duty notes is that the computer software program will allow for the user to directly, securely, and electronically send their notes in a portable file to a third party reimbursement entity and/or billing system or business that exists or has yet been discovered. This action will be done after the user has registered their respective software with the third party reimbursement entity to create the direct, secure, and electronic linkage.

The computer software program will have an application that allows for the user to create a direct, secure, and electronic linkage to any insurance board, health insurance company, HMO, PPO, billing company and/or any sort of insurance or billing entity that exists or has yet been discovered that will send their completed notes as a portable file to said third parties and/or billing entities. This process expedites the process of billing for services rendered. This application also is environmentally sound in that there is no paper used in the keeping of client records or sending them via mail to third party reimbursement entities. This direct, secure, an electronic link to third party reimbursement entities via the computer software program and applications within it must be secure to protect the confidentiality of clients and other associated professional duties. This protection of data and secure transfer can be done using any method that exists or has yet been discovered and one such embodiment of a method could be but is not limited to a secure web-based interface between the computer software program and the third party reimbursement entity that has password protection. Another such method could possibly be registering with a third party reimbursement entity to allow such transactions of notes and data to occur using the computer software program and its applications and/or any other sort of registration and allowance of electronic transfer of data in a portable file through secure means via internet based interfaces that exist or have yet been discovered.

As a mental health professional is accepted as a member of an insurance board for either public or private entities associated with healthcare and third party reimbursement entity, then an application within the computer software program would allow the professional to register with said entity to create a direct, secure, and electronic linkage between the computer software program and its applications, the user and/or mental health professional, and the entity to expedite the process of billing and reimbursement.

The computer software program can allow for a mental health professional to track and create portable file pertaining to certain professional duties, responsibilities, memberships, licensures, specializations, certifications, accreditations, competencies, Continuing Education Units, and/or any other sort of professional activities and/or duties associated with the maintaining of mental health professional, legal, and/or ethical duties and responsibilities. Mental health professionals are expected to be members of various organizations in order to uphold a high level of professionalism and continuing their education throughout their career. Some of these organizations include the American Counseling Association (ACA) and all of its divisions, branches, and affiliates, the American Psychological Association (APA) and all of its divisions, branches and affiliates, the American Psychiatric Association (APA) and all of its divisions, branches, and affiliates, the Council for Accreditation of Counseling and Related Educational Programs (CACREP) and all of its divisions, branches, and affiliates, the National Association of Social Workers (NASW) and all of its divisions, branches and affiliates, the American Association of State Counseling Boards (AASCB) and all of its divisions, branches, and affiliates, the American Association of Marriage and Family Therapists (AAMFT) and all of its divisions, branches, and affiliates, that National Association of School Psychologists (NASP) and all of its divisions, branches, and affiliates, the American Medical Association (AMA) and all of its divisions, branches, and affiliates, the American Psychiatric Nurses Association (APNA) and all of its divisions, branches, and affiliates, and/or any other professional organization, institution, entity, and/or business associated with mental health professionals that exists or has yet been discovered. Mental health professionals have to pay dues to keep their membership up-to-date and provide evidence that they are meeting responsibilities that uphold their professional standing such as continuing education units and attendance to certain professional mental health functions. An application within the computer software program will allow them to track their membership status, maintenance of that status, pay fees, and keep track of the CEUs in order to keep their memberships valid. This application will allow for users to enter data about CEU training sessions and professional activities that they have attended into portable files as well as the evidence provided to them that proves that they did indeed attend and complete all duties and responsibilities associated with their continuing education and professional activities. Once the user has collected enough CEUs and/or professional trainings to meet their obligations to their professional organizations then an application within the computer software program will allow them to directly, securely, and electronically send a portable file containing the information to said organization, institution, entity, and/or business through a direct, secure, and electronic linkage showing that they have met their professional obligations. This application is very useful to mental health professionals wanting to keep track of their CEUs, activities, and memberships to professional organizations and expedites the process of sending their data in a portable file to said organizations through direct, electronic, and secure means. The application within the computer software program will have direct, secure, and electronic linkages to said professional organizations via password security, registering through the computer software program with said organizations, and secure transmission of data via the internet or interface and/or by any process that exists or has yet been discovered. All data entered into this application of the computer software program will be saved either to a computer's hard drive and/or any memory storage device as a portable file. The process of saving the portable file to a computer's hard drive and/or any other kind of memory storage device can be done by any means that exists or has yet been discovered. This application can also be used to track and monitor status in terms of upholding certifications, licensures, specializations, and accreditations that exist in mental health fields and also directly, electronically, and securely sending data in a portable file to any organization that exists or has yet been discovered that monitors and provides professional certifications, licensures, specializations, and accreditations within mental health fields. Such organizations include the National Board of Certified Counselors (NBCC) and all of its divisions, branches, and affiliates, the Commission of Rehabilitation Counselor Certification (CRCC) and all of its divisions, branches, and affiliates, the Commission on Accreditation for Marriage and Family Therapy Education (COAMFTE) and all of its divisions, branches, and affiliates, the Council for Higher Education Accreditation (CHEA) and all of its divisions, branches, and affiliates, the Council on Rehabilitation Education (CORE) and all of its divisions, branches, and affiliates, state licensing boards for all states, and any other sort of professional institution or organization that certifies, licenses, credentials, accredits, or gives specializations in any mental health profession or educational program that exists or has yet been discovered. The computer software program will provide the user with direct, secure, and electronic linkages with said organizations and institutions so that the user can enter and save data in a portable file about their professional activities and responsibilities to maintain their licenses, certifications, specializations, and accreditations such as CEUs, supervision, client hours, competencies, education, and any other sort of responsibility that exists or has yet been discovered and then send the information to said organizations via the application in the computer software program. The user can keep a running total of hours and activities spent meeting requirements of their affiliations with said organizations and institutions over the span of their career and send the data and evidence as a portable file to the organizations and institutions as needed using the applications within the computer software program.

Mental health professionals administer and interpret empirically-based assessments and evaluations. Mental health professionals must have the proper training and education to give certain kinds of assessments and evaluations and must obtain them from publishing companies and/or the creators of said assessments and evaluations. There are three levels of assessments and evaluations, Level A, Level B, and Level C. Mental health professionals with little formal education and bachelor's degrees can give Level A assessments. Professionals with Master's level education can give some Level B assessments with some practical knowledge and experience. Level C assessments are more complex and mental health professionals must have extensive training and experience and be qualified and often times certified to give these complex assessments as well as have an advanced degree such as a PhD, MD, and/or other highly advanced degrees that exist. This computer software program will allow for a user to have direct, secure, and electronic access to publishing companies and licensors of formal evaluations and assessments that they are qualified to administer and interpret to their clients. Furthermore, a user of the computer software program will be able to purchase and/or download various assessments using direct, secure, electronic linkages with the publishers of assessments and evaluations as well as have access to assessments and evaluations for all differing kinds of formal assessment that exist or have yet been discovered. Users will register their software with various publishers and/or owners of assessments and evaluations to establish a direct, secure, and electronic linkage with said publishers and/or owners. Users must verify through the direct, secure, and electronic linkage that they are certified for administering and interpreting the specific levels of assessments and evaluations that they requesting through registering themselves via the computer software program and its applications with said publishers and their credentials and training with said assessments and evaluations. This can be done by using an application within the computer software program that allows for a user to enter relevant information and data as a portable file about their professional credentials and education in the administering and interpretation of said assessments and evaluations. The mental health professional will then send it to publishers and owners of said assessments and evaluations in a portable file as they attempt to both register and purchase said assessments and evaluations using the computer software program. Once the direct, secure, and electronic linkage and registration has been facilitated between the publishers and owners of said assessments and evaluations then the user will have said assessments and evaluations sent to them electronically or shipped to them so that they can be administered. This process allows for quick and efficient access to evaluations and assessments. The procurement and utilization of assessments and evaluations by credentialed and certified professionals is more streamlined and efficient. Publishers and/or owners also have the ability to maintain and assure that their assessment and evaluation rights are being upheld. The computer software program will have applications that allow for users to upload their credentials and competencies in administering and interpreting assessments and evaluations into portable files, create direct, secure, and electronic linkages with publishing companies and/or owners of assessments and evaluations, and purchase and/or utilize said assessments and evaluations electronically using the computer software program and its applications.

The registration and direct, secure, and electronic linkages with professional organizations and institutions within mental health fields will allow for a mental health professional using the computer software program to be sent information and advertisements relevant to their professional practice. Once a user has registered and uploaded data about their memberships, licenses, certifications, credentials, accreditations, experience, and/or any other sort of professional relevant data with the various organizations and institutions that they are a part of using applications within the computer software program, then said organizations and institutions will be able to send information about services, products, CEU opportunities, updates, and/or any other sort of relevant mental health professional information or advertisements that exist or have yet been discovered using the direct, secure, and electronic linkages made by the computer software program. This will allow for businesses, institutions, and/or organizations affiliated and/or concentrated within mental health fields to provide their target audiences, mental health professionals, with information about opportunities for credentials, specializations, licenses, accreditations, certifications, CEU credits, products, conferences, job postings, education opportunities, memberships, and/or any other sort of product, service, and/or advertisement that exists or has yet been discovered associated with professional mental health. The computer software program provides a medium and platform for mental health oriented entities, businesses, organizations, and institutions to advertise and inform mental health professionals about opportunities relevant to their professional practice and growth. Said entities, businesses, organizations, and/or institutions will pay the licensors of the computer software program and its applications to be able to advertise and/or send information to mental health professionals that are and/or are not registered with their respective entities, businesses, organizations, and/or institutions.

A user of the computer software program and its applications will be able to access information about multicultural issues, diagnostic information within the DSM-IV-TR, formal evaluation and assessment, statistics, ethics, legal statutes, professional organizations and memberships, licensures, certifications, accreditations, medications, psychopharmacology, theoretical orientations, developmental issues, professional issues, research, vocational information, therapeutic interventions, therapy notes, educational information, Continuing Education Unit opportunities, consultation, professional discourse and communication, supervision practices and regulations, and/or any other sort of information related to the professional practice and duties of a mental health professional using the computer software program. Applications within the computer software program will allow for users to be able to access information about all of the relevant issues that mental health professionals must be competent of to maintain professional, ethical, competent, and legal practice. Previous research and information based on all of these mental health constructs and practices will be included within the computer software program. The user will be able to access this information which will be preinstalled within the computer software package by clicking on a link that denotes each area of mental health practice and/or be provided with internet hyperlinks installed into the computer software program that will allow them to access the information. This information will be created and preinstalled into the computer software program and its applications and can come from any existing publication, research, and/or body of knowledge that exists or has yet been discovered that is relevant to professional mental health practice and competency.

The user of the computer software program will be able to register with research journals, databases, and/or any other sort of business, organization, and institution that publishes and/or presents research and information about professional mental health facilitation and research using applications within the computer software package. The computer software package will allow for a user to create secure, direct, and electronic linkages with said businesses, organizations, and/or institutions that publish or present data and research on related and relevant professional mental health practice upon registering with said entities and paying for access and/or a subscription to their magazine, journal, database, and/or any other sort of medium that exists or has yet been discovered through a direct, secure, and electronic linkage that is created by registering with said entity.

The computer software program and its applications will allow for a mental health professional to conduct statistical analyses on relevant professional, business, and therapeutic activities associated with their professional practice and tracking of data. The computer software program will have applications that will convert the data entered by the mental health professional about their professional activities into statistical outputs. Any statistical technique that exists or has yet been discovered can be used within the computer software program and includes but is not limited to descriptive statistics, inferential statistics, business planning, business expenses, business incomes, taxes, and/or any other kind of professional functioning and/or activity that could necessitate the use of statistical analyses to gain information on using the computer software program and its applications.

The computer software program and its applications will allow monetary and credit transactions to occur when a mental health professional needs to make secure transactions for mental health related business and/or professional activities. The mental health professional will register with the various mental health oriented organizations, institutions, entities, and/or businesses they are affiliated with using the computer software program and its applications to create direct, secure, and electronic linkages with said organizations, institutions, entities, and/or businesses that will allow the mental health professional to facilitate secure monetary and credit transactions between themselves and said organizations, institutions, entities, and/or businesses using the computer software program and its applications. Part of registering using the computer software program and its applications would be for a mental health professional to enter data about their various bank accounts and/or lines of credit in a secure and protected manner into a portable file within the computer software program so that the facilitation of conducting monetary and/or credit transactions can be done directly, securely, and electronically by the linkage between the professional and organizations, institutions, entities, and/or businesses.

OPERATION OF INVENTION

FIGS. 1, 2A, 2B, 2C, 2D, 3, 4, 5A, 5B, 5C, 5D, 6, 7, 8A, 8B, 8C, 8D, 8E, 8F, 9A, 9B, 9C, and 9D FIG. 1. The mental health professional (101) uses the computer software program and its applications (102) that contains note templates (103) that are either created by the user or are preinstalled (104) or uploaded into the computer software program (102) and enters data (105) onto the note template (103) and saves (106) it to a storage device (107) that exists or has yet been discovered. The mental health professional (101) then registers (108) with a health insurance company, insurance board, insurance company, HMO, PPO, billing agency, third-party reimbursement company and/or entity (109) that exists or has yet been discovered that they are seeking reimbursement for professional services rendered using the computer software program and its applications (102) to create a direct, secure, and electronic linkage (110) with said entity (109). The mental health professional (101) then sends the data (105) on the note templates (103) created by the computer software program and its applications (102) to the insurance entity (109) via the direct, secure, and electronic linkage (110) created by the computer software program and its applications (102). The entity (109) then approves the data (105) and sends reimbursement (111) to the mental health professional (101) via the direct, secure, and electronic linkage (110) created by the computer program and its applications (102) by any electronic fund transfer solution (112) that exists or has yet been discovered that the computer software program and its applications (102) creates through registration (108) and linkages (110) between the mental health professional (101) and the entity (109).

FIG. 2A. One can see how mental health related professional organizations (201), professional conferences (202), professional meetings (202), professional presentations (202), Continuing Education Units (CEUs) opportunities (203), hospitals (204), private practices (204), and treatment centers (204) can advertise and/or send information (216) within the computer software package and its applications (102) that create a direct, secure, and electronic linkage (110) to reach their target audiences such as mental health professionals (101) who utilize the computer software program and its applications (102). The various entities, products, and services (201)-(204) can either pay (217) to have access to advertise (216) within the computer software program and its applications (102) and/or the mental health professional (101) utilizing the computer software program and its applications (102) can register (108) with the various entities, products, and services (201)-(204) they will allow to send them information and/or advertisements (216) by registering (108) their computer software program and applications (102) to create a direct, secure, and electronic linkage (110) between themselves (101) and said entities, products, and services (201)-(204) using the computer software program and its applications (102).

Figure 2B:
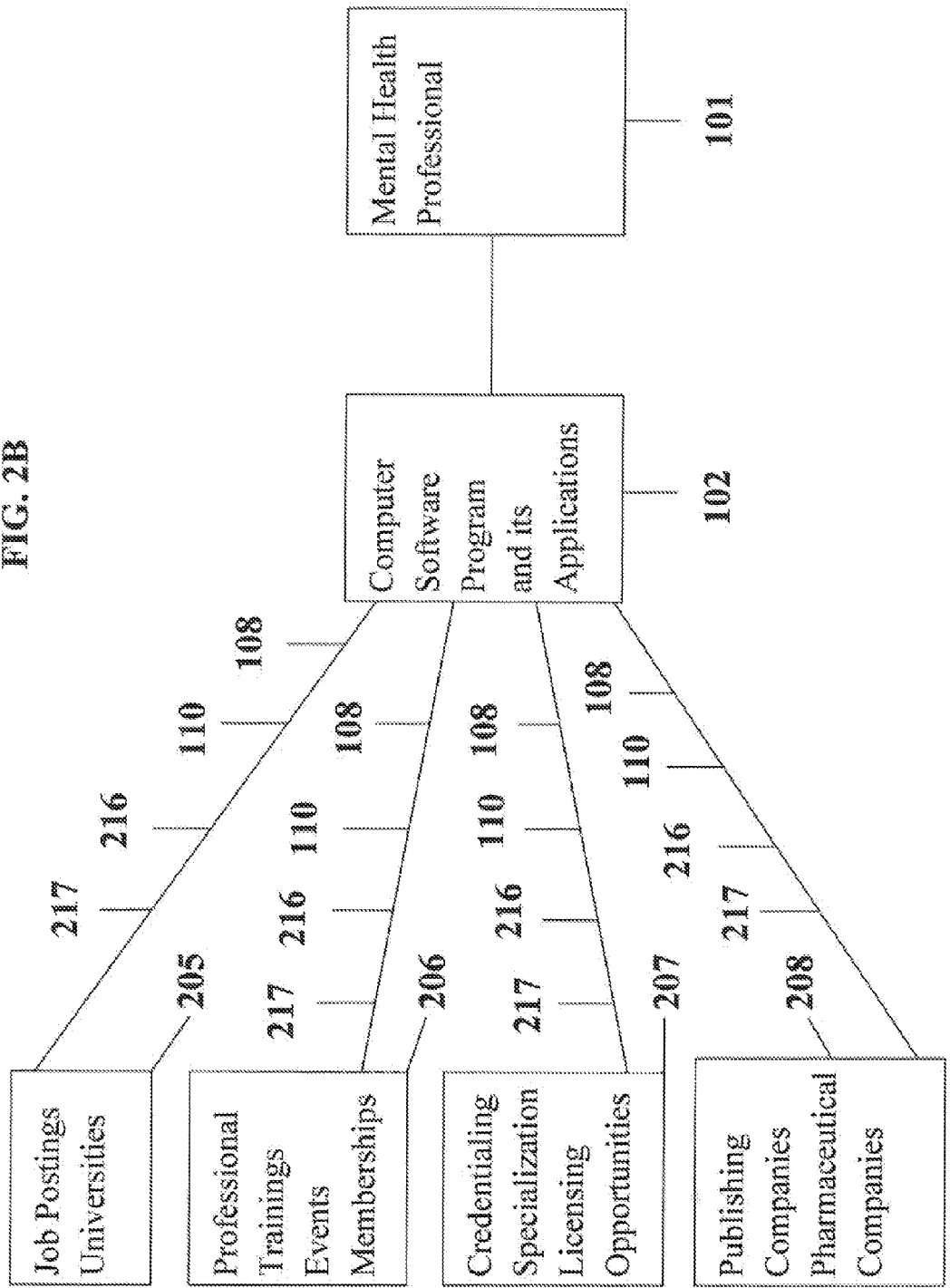

FIG. 2B. One can see how job postings (205), universities (205), professional trainings (206), professional events (206), professionals memberships (206), credentialing opportunities (207), specialization opportunities (207), licensing opportunities (207), publishing companies (208), pharmaceutical companies (208) can advertise and/or send information (216) within the computer software package and its applications (102) that create a direct, secure, and electronic linkage (110) to reach their target audiences such as mental health professionals (101) who utilize the computer software program and its applications (102). The various entities, products, and services (205)-(208) can either pay (217) to have access to advertise (216) within the computer software program and its applications (102) and/or the mental health professional (101) utilizing the computer software program and its applications (102) can register (108) with the various entities, products, and services (205)-(208) they will allow to send them information and/or advertisements (216) by registering (108) their computer software program and applications (102) to create a direct, secure, and electronic linkage (110) between themselves (101) and said entities, products, and services (205)-(208) using the computer software program and its applications (102).

Figure 2C:
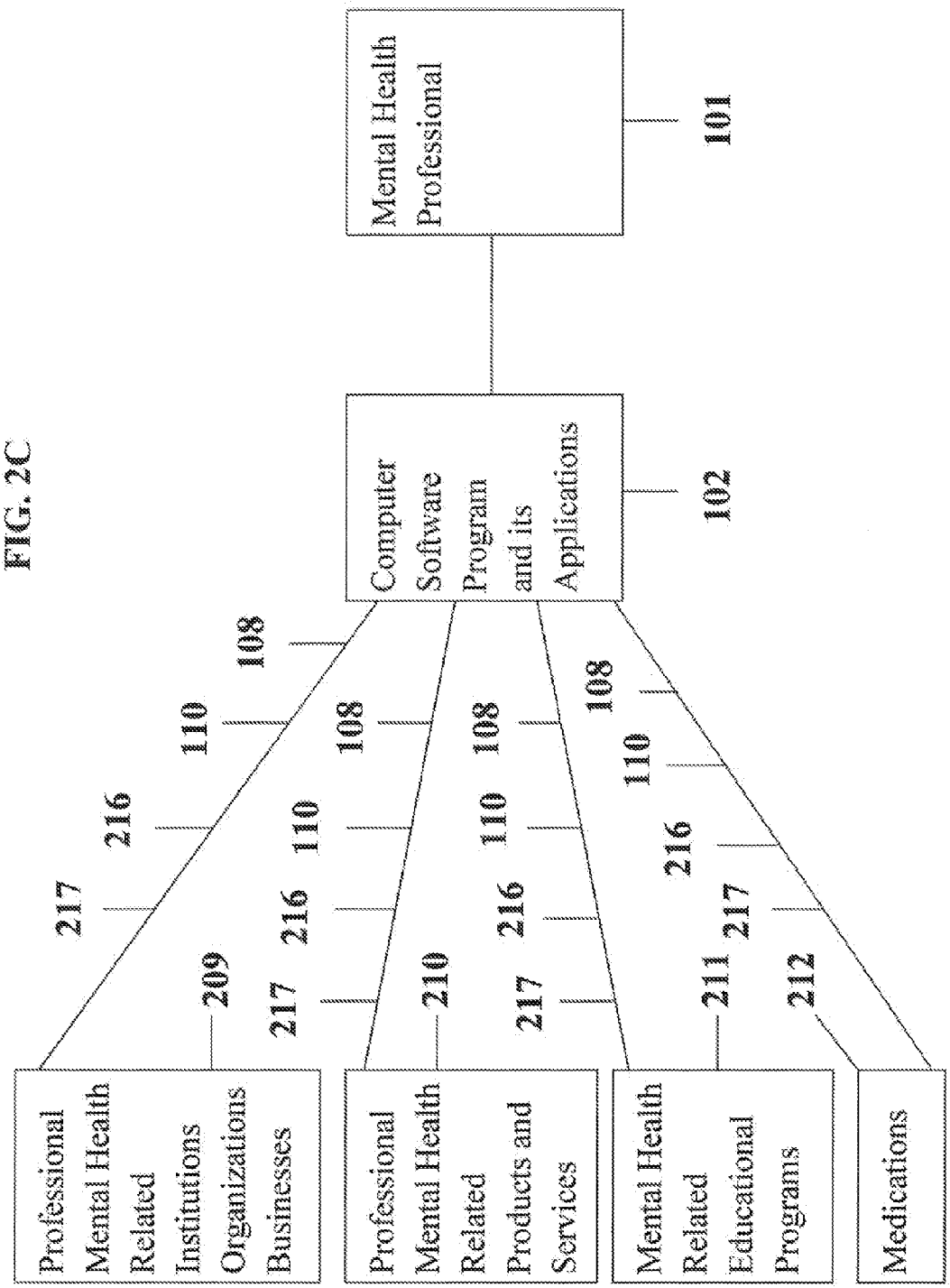

FIG. 2C. One can see how professional mental health related institutions (209), businesses (209), and/or organizations (209), professional mental health related products and services (210), mental health related educational programs (211), medications (212) can advertise and/or send information (216) within the computer software package and its applications (102) that create a direct, secure, and electronic linkage (110) to reach their target audiences such as mental health professionals (101) who utilize the computer software program and its applications (102). The various entities, products, and services (209)-(212) can either pay (217) to have access to advertise (216) within the computer software program and its applications (102) and/or the mental health professional (101) utilizing the computer software program and its applications (102) can register (108) with the various entities, products, and services (209)-(212) they will allow to send them information and/or advertisements (216) by registering (108) their computer software program and applications (102) to create a direct, secure, and electronic linkage (110) between themselves (101) and said entities, products, and services (209)-(212) using the computer software program and its applications (102).

FIG. 2D. One can see how journals (213), databases (213), research (213), books (213), assessments and evaluations (214), and/or any other sort of mental health related products or services that exist or yet has been discovered (215) can advertise and/or send information (216) within the computer software package and its applications (102) that create a direct, secure, and electronic linkage (110) to reach their target audiences such as mental health professionals (101) who utilize the computer software program and its applications (102). The various entities, products, and services (213)-(215) can either pay (217) to have access to advertise (216) within the computer software program and its applications (102) and/or the mental health professional (101) utilizing the computer software program and its applications (102) can register (108) with the various entities, products, and services (213)-(215) they will allow to send them information and/or advertisements (216) by registering (108) their computer software program and applications (102) to create a direct, secure, and electronic linkage (110) between themselves (101) and said entities, products, and services (213)-(215) using the computer software program and its applications (102).

FIG. 3. The mental health professional (101) will enter data (105) into the computer software program and its applications (102) about their credentials and training relevant to the administration and interpretation of all levels of assessment and evaluation within professional mental health (301). The direct, secure, and electronic linkages (110) created by the computer software program and its applications (102) by the mental health professional (101) registering (108) their credentials (301) with various mental health related entities that publish, own, and/or copyright assessments and evaluations (214) will allow for the mental health professional (101) to access, purchase, and/or utilize (302) assessments and evaluations that their credentials and training will allow for them to using the computer software program and its applications (102) and for publishers and/or owners (303) to send (216) assessments and evaluations (214) electronically through the created linkages (110) to the mental health professional (101) through the computer software program and its applications (102) so they can be utilized for clients and professional mental health activities.

Figure 4:
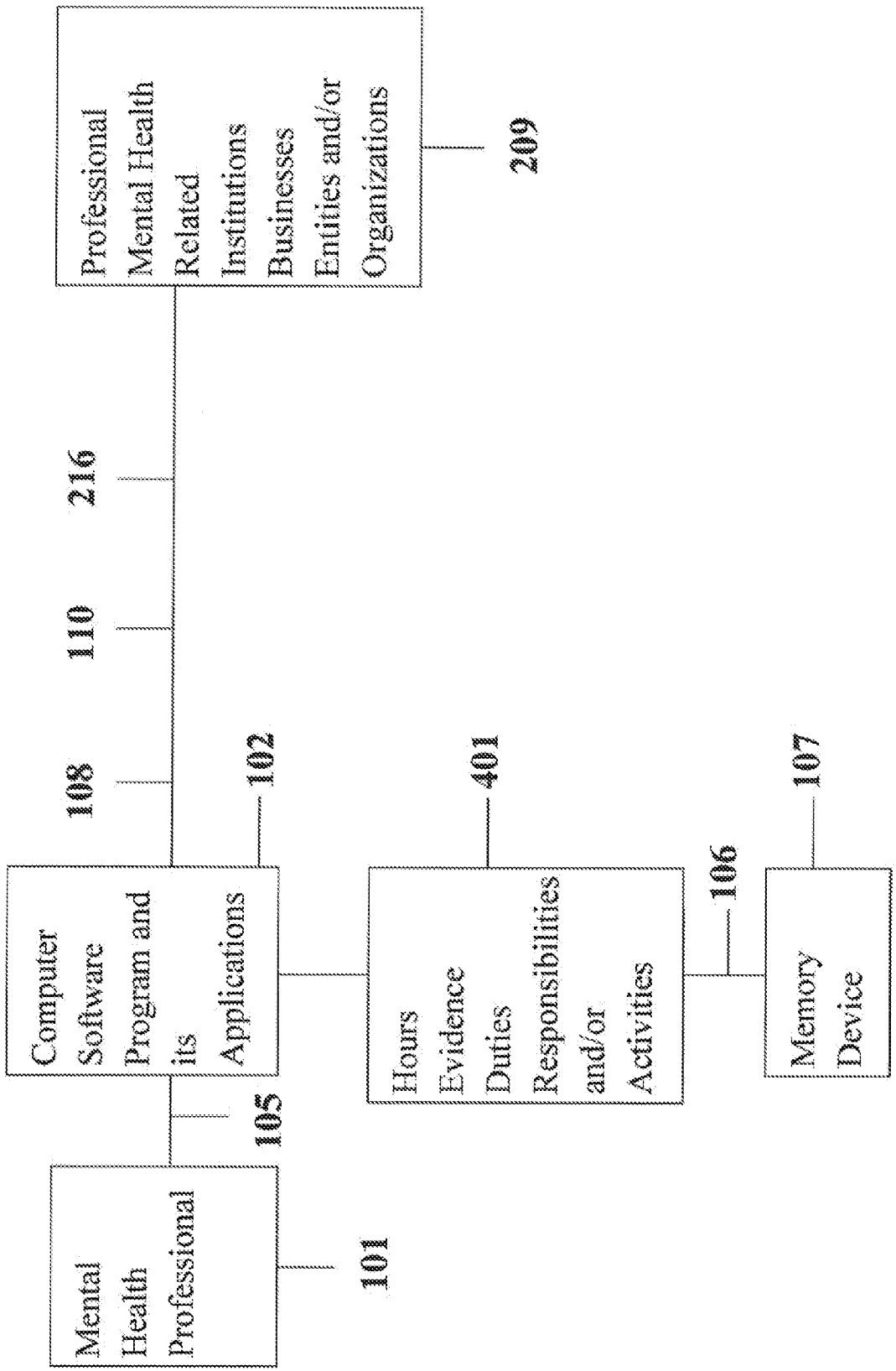
FIG. 4. This figure depicts how a user of the computer software program and its applications can track and update the responsibilities inherent in obtaining and maintaining licensure, certification, CEUs, accreditation, specialization, credentials, professional organizations and memberships, and insurance reimbursement within professional mental health practice.

FIG. 4. The mental health professional (101) registers (108) with the various professional mental health organizations, institutions, entities, and/or businesses they are associated with (209) using the computer software program and its applications (102) to create a direct, secure, and electronic linkage (110) with said organizations, institutions, entities, and/or businesses (209). The mental health professional (101) would then use an application within the computer software program (102) that allows the mental health professional (101) to enter data (105) and keeps a running total of hours, evidence, and/or activities (401) they complete to meet the requirements associated with maintaining the professional standards of said organizations, institutions, entities, and/or businesses (209) by entering data (105) and evidence of their hours and/or activities into the computer software program (102) and saving (106) the data (105) to a memory device that exists or yet has been discovered (107). When the mental health professional (101) meets the requirements associated with their affiliation and/or membership with said entities that certify, credential, license, accredit, and/or reimburse (209), then they will be able to use the computer software and its applications (102) to send (216) the data (105) they have tracked on their professional activities, duties, and/or responsibilities (401) to said entities (209) via the direct, secure, and electronic linkage (110) created by the computer software and its applications (102) to provide evidence of said activities, duties, and/or responsibilities (401) and maintain their certifications, credentials, licenses, accreditations, and/or ability to obtain reimbursement.

Figure 5A:
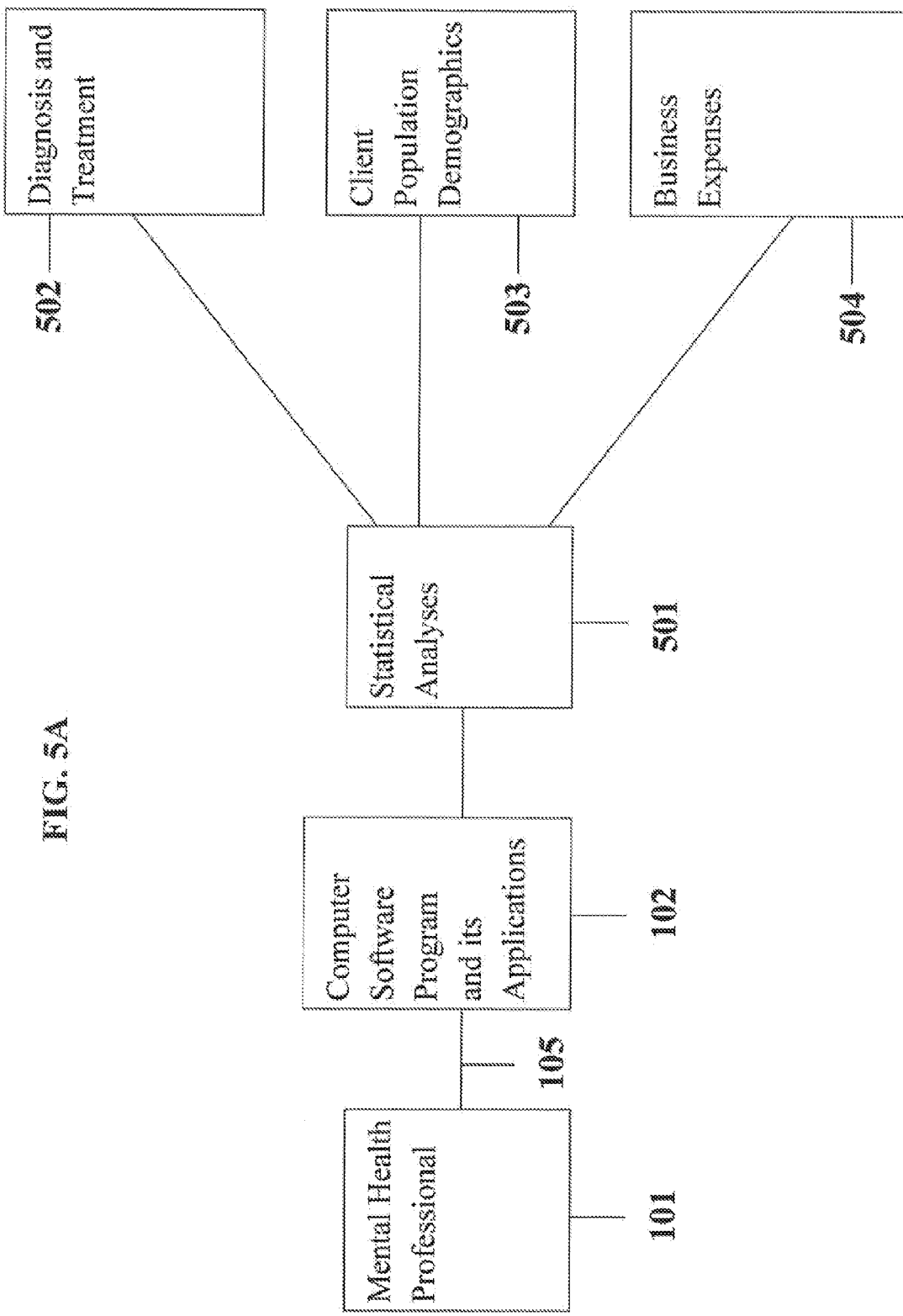
FIGS. 5A, 5B, 5C, and 5D. These figures depict how the computer software program and its applications can provide statistical analyses on relevant professional mental health information and activities.

FIG. 5A. The computer software program will have applications (102) that can provide the mental health professional (101) with statistical analyses (501) tracking their personal trends in diagnosis and treatment (502), client population demographics (503), business expenses (504). The computer software program and its applications (102) can conduct any sort of statistical analysis that exists or has yet been discovered (501) and includes but is not limited to descriptive statistics, inferential statistics, business planning, business expenses, business incomes, taxes, and/or any other kind of professional functioning and/or activity that could necessitate the use of statistical analyses to gain information on using the computer software program and its applications. The mental health professional (101) will enter data (105) about their professional functions and/or activities (502)-(504) and the computer software program (102) will take the entered data (105) and use applications that conduct statistical analyses (501) on the entered data (105) to provide quantitative data about said functions and/or activities (502)-(504) that the mental health professional (101) will be able to save, record, and/or utilize.

Figure 5B:
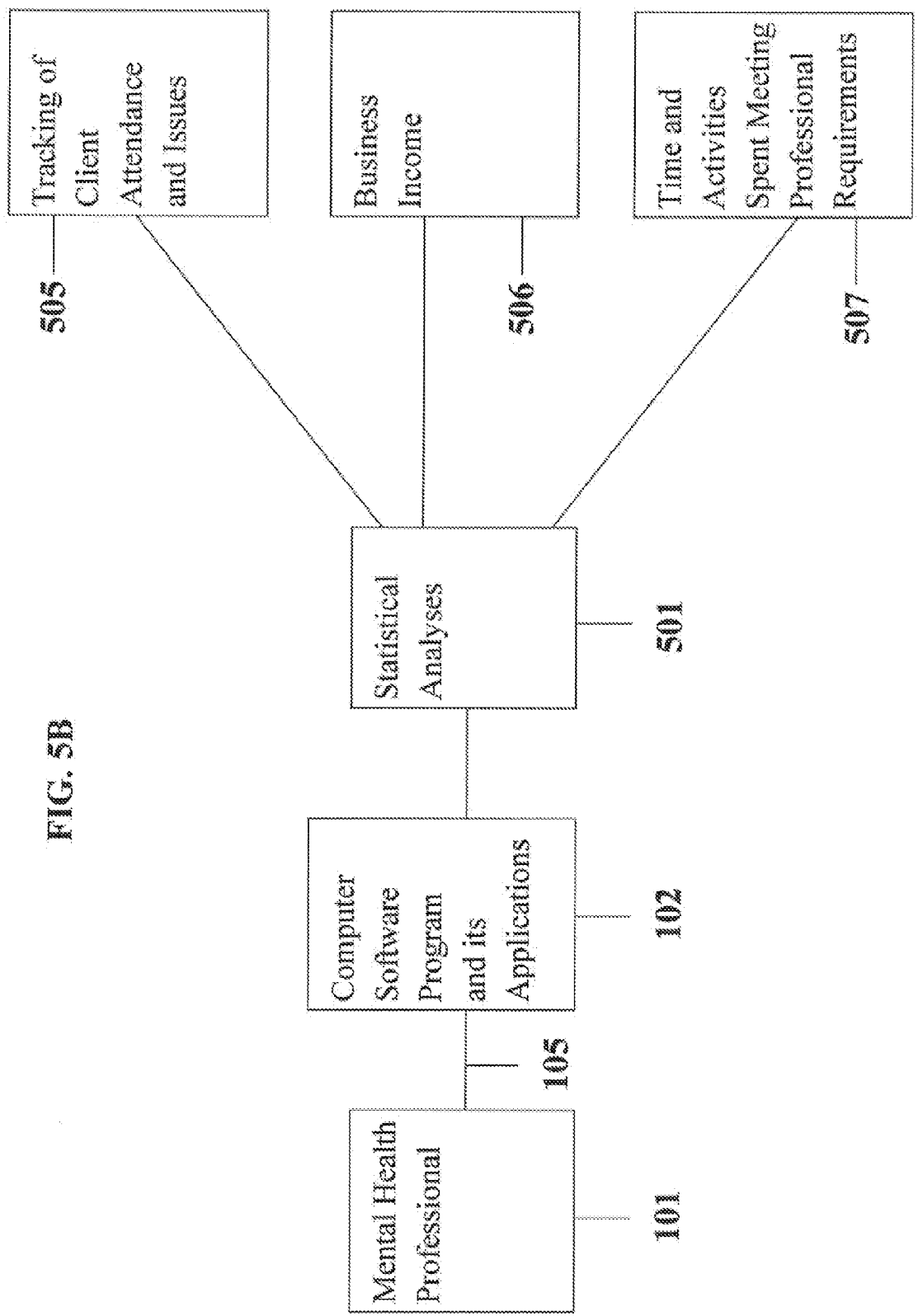

FIG. 5B. The computer software program will have applications (102) that can provide the mental health professional (101) with statistical analyses (501) tracking their personal trends in tracking of client attendance and issues (505), business income (506), time and activities spent meeting professional requirements (507). The computer software program and its applications (102) can conduct any sort of statistical analysis that exists or has yet been discovered (501) and includes but is not limited to descriptive statistics, inferential statistics, business planning, business expenses, business incomes, taxes, and/or any other kind of professional functioning and/or activity that could necessitate the use of statistical analyses to gain information on using the computer software program and its applications. The mental health professional (101) will enter data (105) about their professional functions and/or activities (505)-(507) and the computer software program (102) will take the entered data (105) and use applications that conduct statistical analyses (501) on the entered data (105) to provide quantitative data about said functions and/or activities (505)-(507) that the mental health professional (101) will be able to save, record, and/or utilize.

Figure 5C:
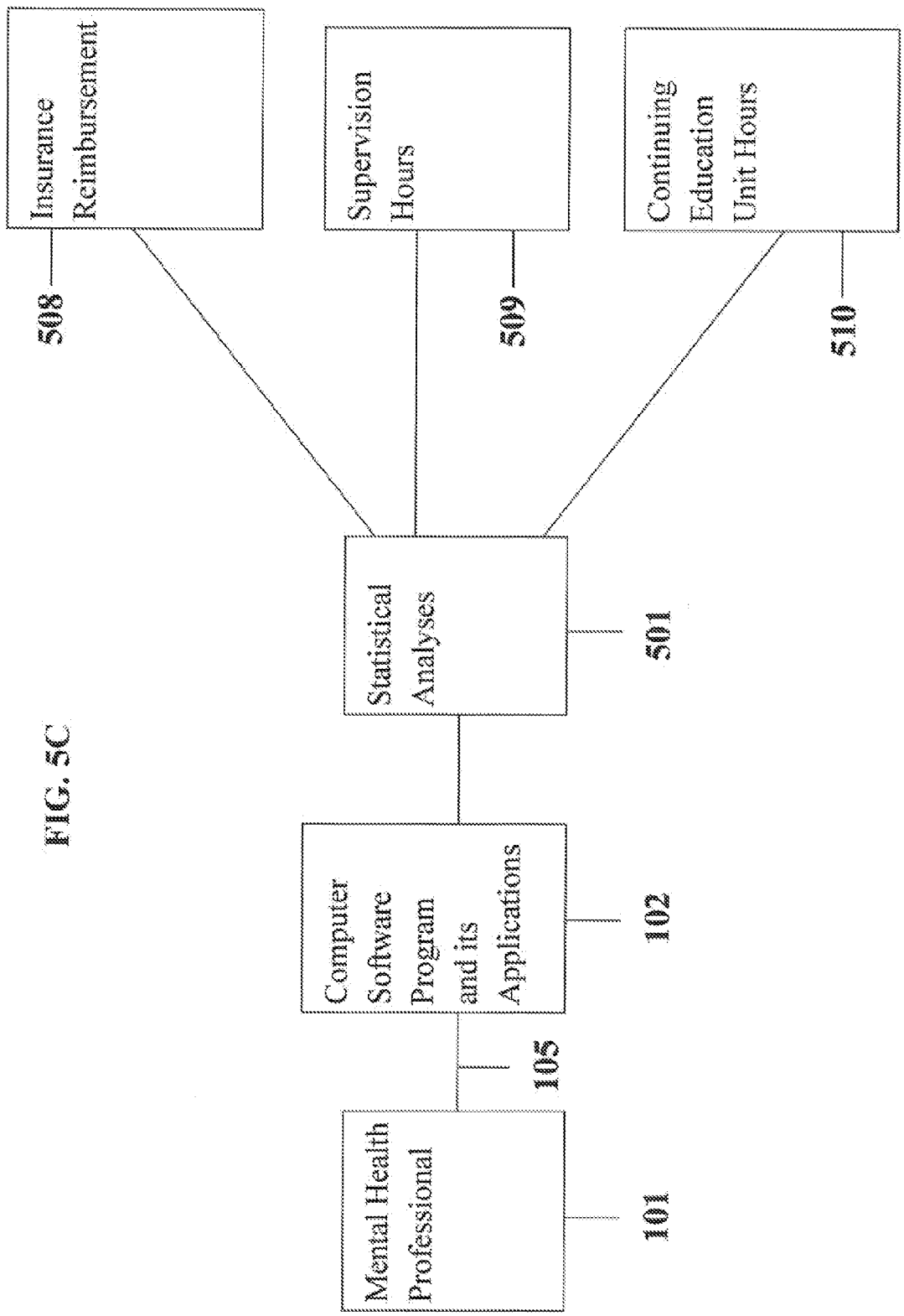

FIG. 5C. The computer software program will have applications (102) that can provide the mental health professional (101) with statistical analyses (501) tracking their personal trends in insurance reimbursement (508), supervision hours (509), CEU hours (510). The computer software program and its applications (102) can conduct any sort of statistical analysis that exists or has yet been discovered (501) and includes but is not limited to descriptive statistics, inferential statistics, business planning, business expenses, business incomes, taxes, and/or any other kind of professional functioning and/or activity that could necessitate the use of statistical analyses to gain information on using the computer software program and its applications. The mental health professional (101) will enter data (105) about their professional functions and/or activities (508)-(510) and the computer software program (102) will take the entered data (105) and use applications that conduct statistical analyses (501) on the entered data (105) to provide quantitative data about said functions and/or activities (508)-(510) that the mental health professional (101) will be able to save, record, and/or utilize.

Figure 5D:
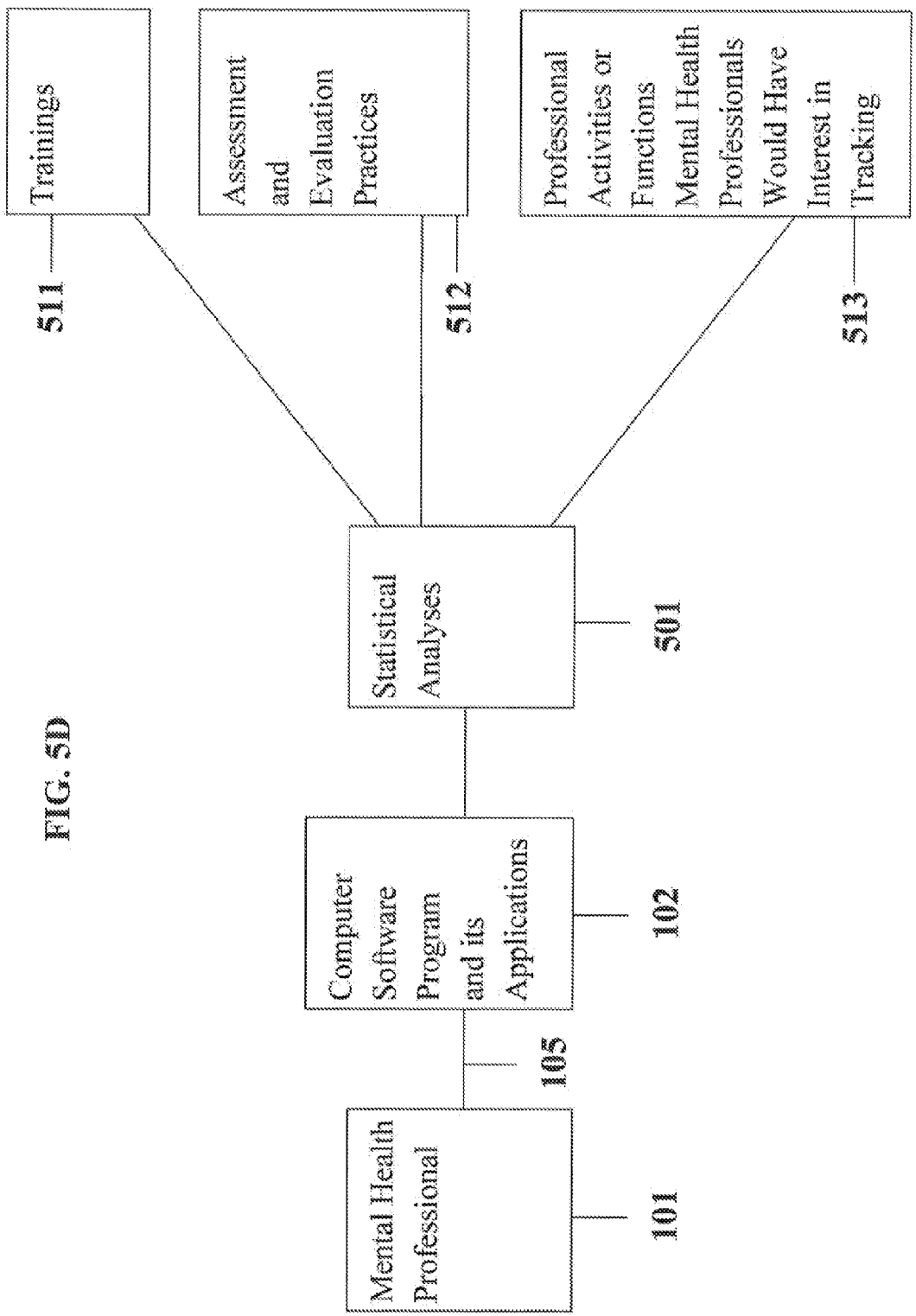

FIG. 5D. The computer software program will have applications (102) that can provide the mental health professional (101) with statistical analyses (501) tracking their personal trends in trainings (511), assessment and evaluation practices (512), and/or any other sort of professional activity and/or function mental health professionals would have interest in tracking via statistical analyses (513). The computer software program and its applications (102) can conduct any sort of statistical analysis that exists or has yet been discovered (501) and includes but is not limited to descriptive statistics, inferential statistics, business planning, business expenses, business incomes, taxes, and/or any other kind of professional functioning and/or activity that could necessitate the use of statistical analyses to gain information on using the computer software program and its applications. The mental health professional (101) will enter data (105) about their professional functions and/or activities (511)-(513) and the computer software program (102) will take the entered data (105) and use applications that conduct statistical analyses (501) on the entered data (105) to provide quantitative data about said functions and/or activities (511)-(513) that the mental health professional (101) will be able to save, record, and/or utilize.

Figure 6:
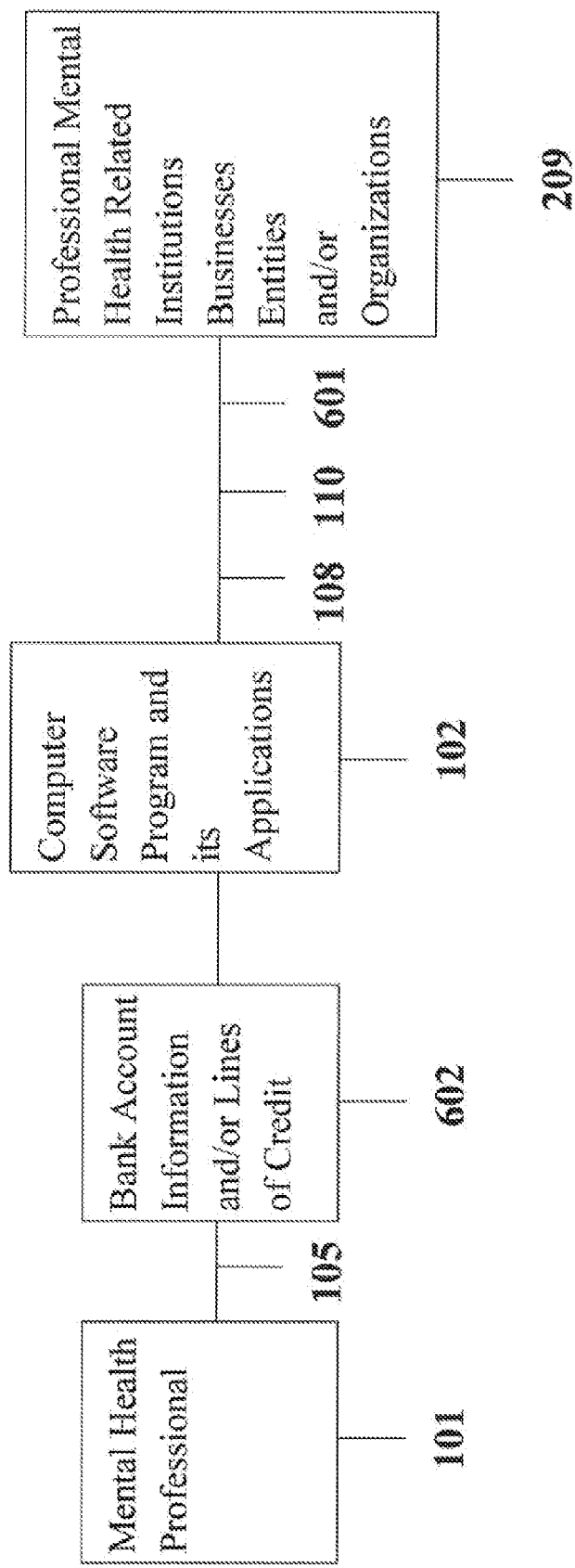
FIG. 6. This figure depicts how monetary and credit transactions can occur within the computer software program when a user needs to make secure transactions for mental health related business and/or professional activities.

FIG. 6. The mental health professional (101) will register (108) with the various professional mental health related organizations, institutions, entities, and/or businesses (401) they are affiliated with using the computer software program and its applications (102) to create direct, secure, and electronic linkages (110) with said organizations, institutions, entities, and/or businesses (401) that will allow the mental health professional (101) to facilitate secure monetary and credit transactions (601) between themselves and said organizations, institutions, entities, and/or businesses (401) using the computer software program and its applications (102). Part of registering (108) using the computer software program and its applications (102) would be for a mental health professional (101) to enter data (105) about their various bank accounts and/or lines of credit (602) in a secure and protected manner into the computer software program so that the facilitation of conducting monetary and/or credit transactions (601) can be done directly, securely, and electronically with the linkage (110) between the professional (101) and organizations, institutions, entities, and/or businesses (401) that is created by the computer software program and its applications (102).

FIG. 7. The mental health professional (101) can register (108) with various publishers and owners of databases, research journals, research, and/or any other sort of publisher of mental health research and information (701) using the computer software program and its applications (102) to create a direct, secure, and electronic link (110) between said publishers and owners (701) and be able to facilitate monetary and/or credit transactions (601) for access (702) to said databases, research journals, research, and/or publications (701) using the entering of data (105) relevant to various bank accounts and/or lines of credit (602) and the created linkages (110) made by the computer software program and its applications (102). Then, an application within the computer software program (102) would allow for the mental health professional (101) to access (702) databases, research journals, research, and/or publications (701) that they have both registered with (108) and paid (601) for access (702) to using the computer software program and its applications (102).

FIG. 8A. This figure depicts how a user (101) of the computer software program and its applications (102) can access information about client populations (801), multicultural issues (802), diagnostic criteria and information (803), and formal evaluation and assessment (804) using the computer software program and its applications (102). The computer software program and its applications (102) will have all this relevant information (801)-(804) preinstalled (104) when a mental health professional (101) purchases the rights (825) to utilize the computer software program and its applications (102). The information (801-804) can come from any number of sources including but not limited to the DSM-IV-TR, mental health related research, current ethics and legal codes, various mental health related professionals organizations, institutions, businesses, publications, and/or entities that exist or have yet been discovered, books and journals, mental health professionals, and/or any other sort of body of knowledge that exists or has yet been discovered that pertains to professional mental health practice and research. An application within the computer software program will also allow for the user to access various internet sites that contain information on any of the above stated topics using hyperlinks.

Figure 8B:
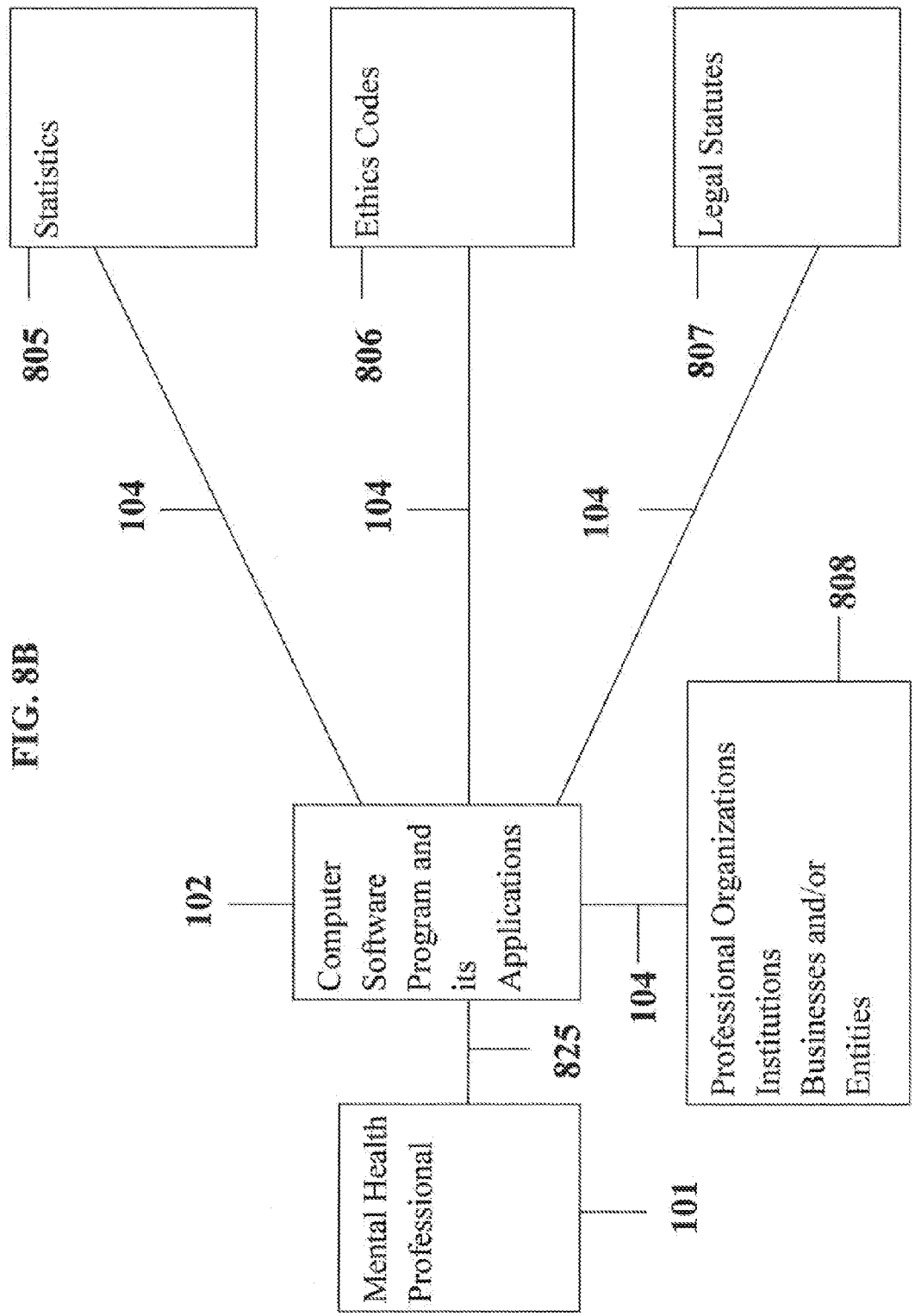

FIG. 8B. This figure depicts how a user (101) of the computer software program and its applications (102) can access information about statistics (805), ethics codes (806), legal statutes (807), professional organizations, institutions, businesses, and/or entities (808) using the computer software program and its applications (102). The computer software program and its applications (102) will have all this relevant information (805)-(808) preinstalled (104) when a mental health professional (101) purchases the rights (825) to utilize the computer software program and its applications (102). The information (805-808) can come from any number of sources including but not limited to the DSM-IV-TR, mental health related research, current ethics and legal codes, various mental health related professionals organizations, institutions, businesses, publications, and/or entities that exist or have yet been discovered, books and journals, mental health professionals, and/or any other sort of body of knowledge that exists or has yet been discovered that pertains to professional mental health practice and research. An application within the computer software program will also allow for the user to access various internet sites that contain information on any of the above stated topics using hyperlinks.

FIG. 8C. This figure depicts how a user (101) of the computer software program and its applications (102) can access information about professional memberships (809), licensures, certifications, accreditations, specializations, and/or credentials (810), medications and/or psychopharmacology (811), therapeutic theoretical orientations (812) using the computer software program and its applications (102). The computer software program and its applications (102) will have all this relevant information (809)-(812) preinstalled (104) when a mental health professional (101) purchases the rights (825) to utilize the computer software program and its applications (102). The information (809-812) can come from any number of sources including but not limited to the DSM-IV-TR, mental health related research, current ethics and legal codes, various mental health related professionals organizations, institutions, businesses, publications, and/or entities that exist or have yet been discovered, books and journals, mental health professionals, and/or any other sort of body of knowledge that exists or has yet been discovered that pertains to professional mental health practice and research. An application within the computer software program will also allow for the user to access various internet sites that contain information on any of the above stated topics using hyperlinks.

FIG. 8D. This figure depicts how a user (101) of the computer software program and its applications (102) can access information about developmental issues and knowledge (813), professional issues and knowledge (814), research (815), vocational information (816) using the computer software program and its applications (102). The computer software program and its applications (102) will have all this relevant information (813)-(816) preinstalled (104) when a mental health professional (101) purchases the rights (825) to utilize the computer software program and its applications (102). The information (813-816) can come from any number of sources including but not limited to the DSM-IV-TR, mental health related research, current ethics and legal codes, various mental health related professionals organizations, institutions, businesses, publications, and/or entities that exist or have yet been discovered, books and journals, mental health professionals, and/or any other sort of body of knowledge that exists or has yet been discovered that pertains to professional mental health practice and research. An application within the computer software program will also allow for the user to access various internet sites that contain information on any of the above stated topics using hyperlinks.

FIG. 8E. This figure depicts how a user (101) of the computer software program and its applications (102) can access information about therapeutic interventions (817), therapy notes and documentation (818), educational information (819), Continuing Education Unit opportunities (820) using the computer software program and its applications (102). The computer software program and its applications (102) will have all this relevant information (817)-(820) preinstalled (104) when a mental health professional (101) purchases the rights (825) to utilize the computer software program and its applications (102). The information (817-820) can come from any number of sources including but not limited to the DSM-IV-TR, mental health related research, current ethics and legal codes, various mental health related professionals organizations, institutions, businesses, publications, and/or entities that exist or have yet been discovered, books and journals, mental health professionals, and/or any other sort of body of knowledge that exists or has yet been discovered that pertains to professional mental health practice and research. An application within the computer software program will also allow for the user to access various internet sites that contain information on any of the above stated topics using hyperlinks.

Figure 8F:
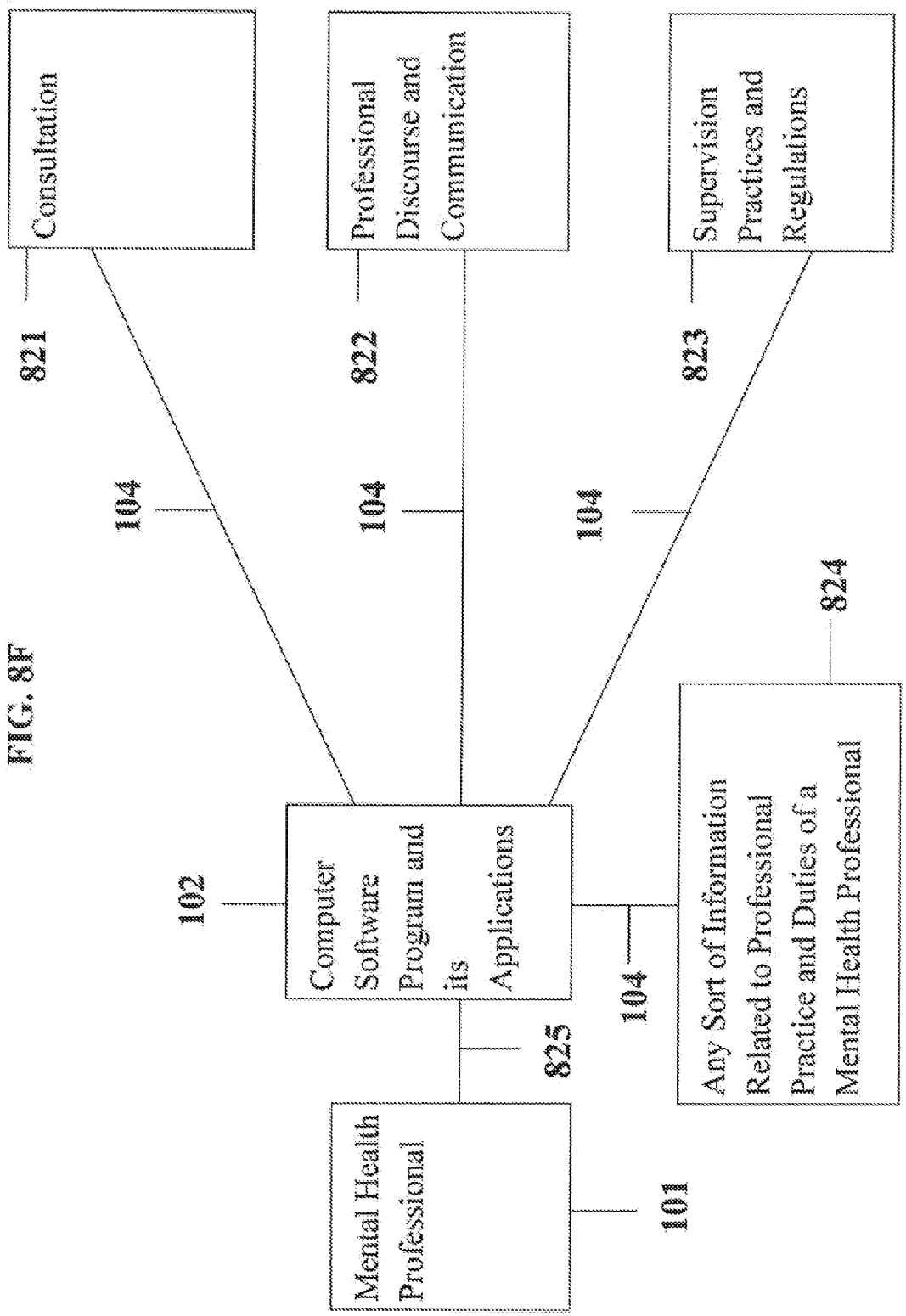

FIG. 8F. This figure depicts how a user (101) of the computer software program and its applications (102) can access information about consultation (821), professional discourse and communication (822), supervision practices and regulations (823), and/or any other sort of information related to the professional practice and duties of a mental health professional that exists or has yet been discovered (824) using the computer software program and its applications (102). The computer software program and its applications (102) will have all this relevant information (821)-(824) preinstalled (104) when a mental health professional (101) purchases the rights (825) to utilize the computer software program and its applications (102). The information (821-824) can come from any number of sources including but not limited to the DSM-IV-TR, mental health related research, current ethics and legal codes, various mental health related professionals organizations, institutions, businesses, publications, and/or entities that exist or have yet been discovered, books and journals, mental health professionals, and/or any other sort of body of knowledge that exists or has yet been discovered that pertains to professional mental health practice and research. An application within the computer software program will also allow for the user to access various internet sites that contain information on any of the above stated topics using hyperlinks.

FIG. 9A. This figure depicts a mental health professional (101) being able to enter data (105) pertaining to their professional information (901) into the computer software program and its applications (102) and saving (106) the data to a memory device (107) as a portable file (902). These portable files (902) can then be sent (216) to various professional organizations, institutions, entities, and/or businesses (209) that the user (101) has registered (108) with via a direct, secure, and electronic linkage (110) between the software program (101) and said organizations, institutions, entities, and/or businesses (209). These portable files can contain information pertaining to notes and documentation (103), licenses (903), credentials (904), specializations (905).

Figure 9B:
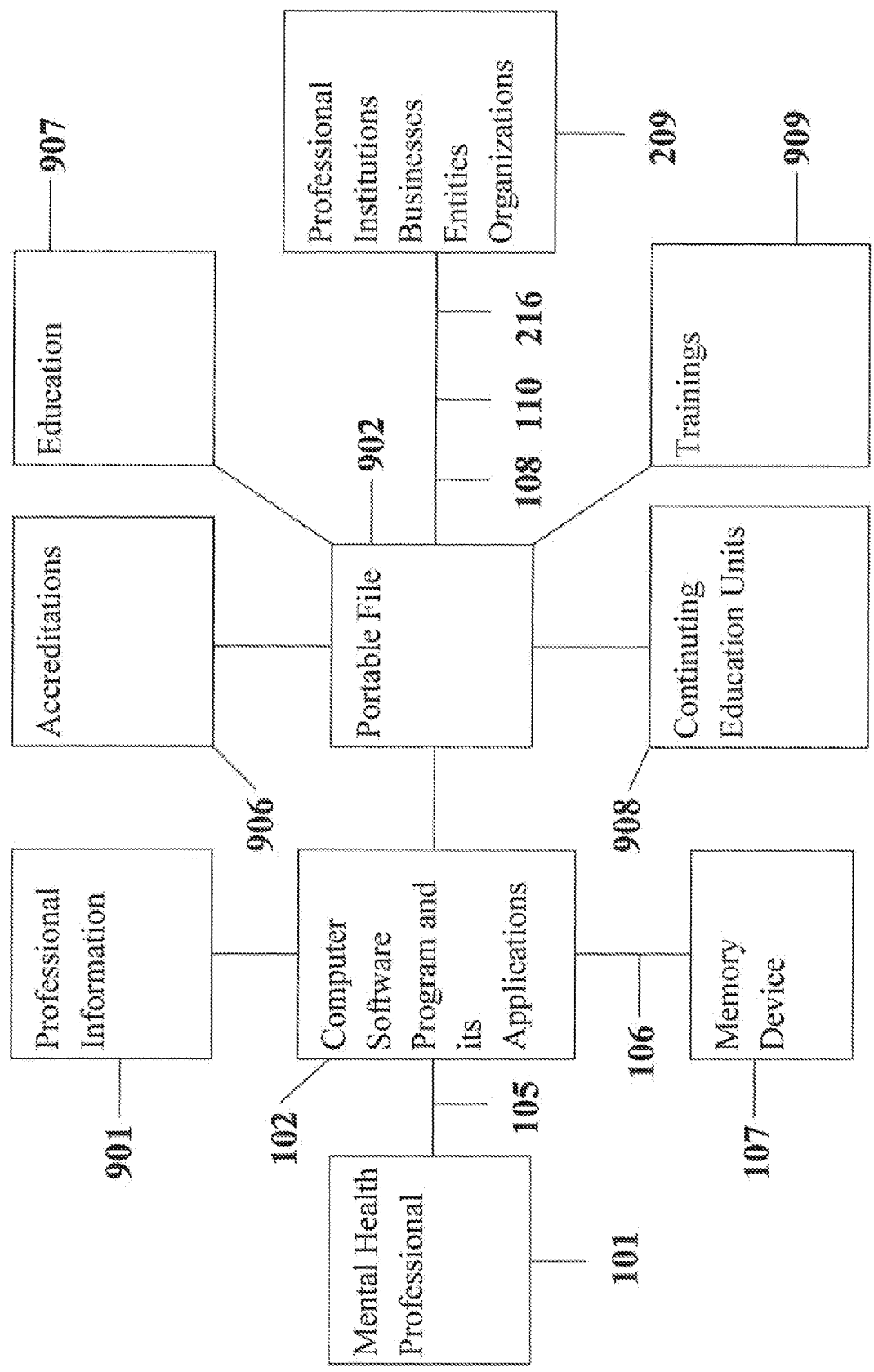

FIG. 9B. This figure depicts a mental health professional (101) being able to enter data (105) pertaining to their professional information (901) into the computer software program and its applications (102) and saving (106) the data to a memory device (107) as a portable file (902). These portable files (902) can then be sent (216) to various professional organizations, institutions, entities, and/or businesses (209) that the user (101) has registered (108) with via a direct, secure, and electronic linkage (110) between the software program (101) and said organizations, institutions, entities, and/or businesses (209). These portable files can contain information pertaining to accreditations (906), education (907), CEUs (908), trainings (909).

Figure 9C:
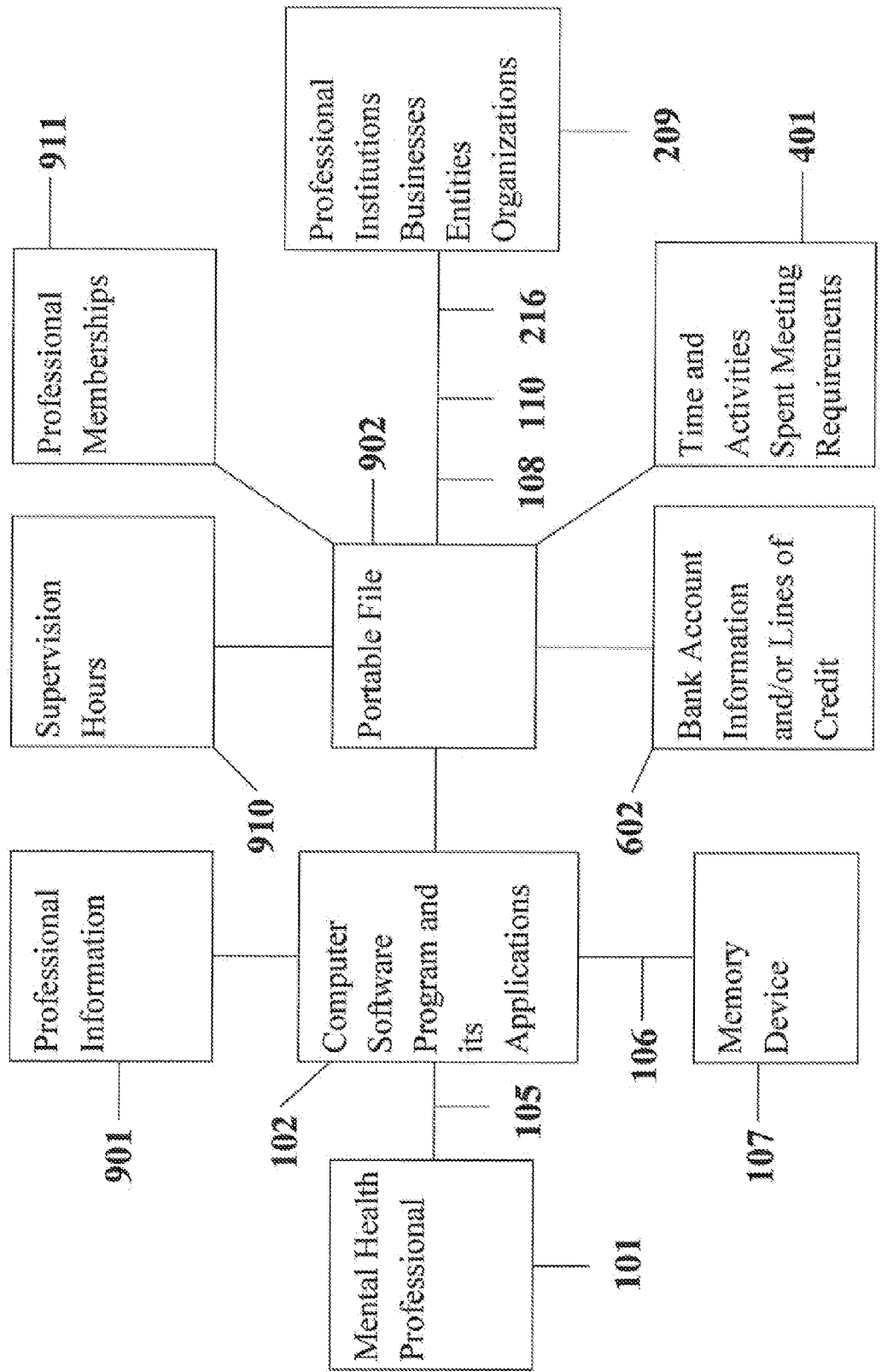

FIG. 9C. This figure depicts a mental health professional (101) being able to enter data (105) pertaining to their professional information (901) into the computer software program and its applications (102) and saving (106) the data to a memory device (107) as a portable file (902). These portable files (902) can then be sent (216) to various professional organizations, institutions, entities, and/or businesses (209) that the user (101) has registered (108) with via a direct, secure, and electronic linkage (110) between the software program (101) and said organizations, institutions, entities, and/or businesses (209). These portable files can contain information pertaining to supervision hours (910), professional memberships (911), bank account information and/or lines of credit (602), time and activities spent meeting requirements (401).

Figure 9D:
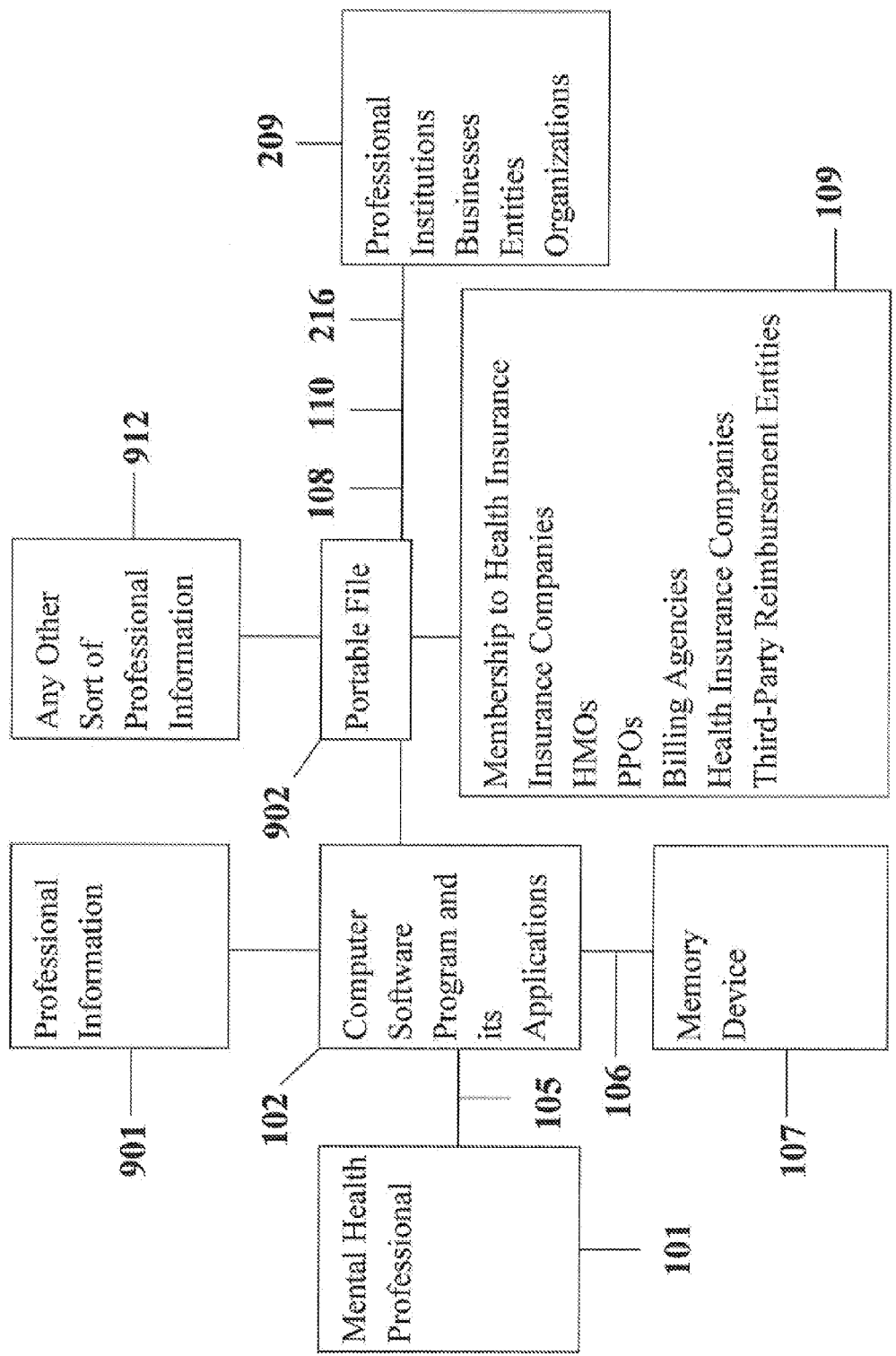

FIG. 9D. This figure depicts a mental health professional (101) being able to enter data (105) pertaining to their professional information (901) into the computer software program and its applications (102) and saving (106) the data to a memory device (107) as a portable file (902). These portable files (902) can then be sent (216) to various professional organizations, institutions, entities, and/or businesses (209) that the user (101) has registered (108) with via a direct, secure, and electronic linkage (110) between the software program (101) and said organizations, institutions, entities, and/or businesses (209). These portable files can contain information pertaining to membership to health insurance boards (109), health insurance companies (109), insurance companies (109), HMOs (109), PPOs (109), billing agencies (109), third-party reimbursement entities (109), and/or any other sort of professional information that can be sent to a professional organization, institution, entity, and/or business (912).

CONCLUSION, RAMIFICATIONS, AND SCOPE OF THE INVENTION

While my above description contains many specificities, these should not be construed as limitations on the scope of the invention, but rather as an exemplification of one preferred embodiment thereof. Some variations could be possible. There are many different software programs targeted towards mental health professionals that have many different applications. There are many different coding languages and schemes that could be used to write the program. There are many ways to install a software program into the memory of a computer. There are many ways to create direct, secure, and electronic linkages between entities. There are many ways to protect transmitted data from one entity to another. There are many different ways to facilitate electronic credit and/or monetary transactions. There are many ways to encrypt data before it is electronically transmitted. There are many ways that entities can advertise and/or send information to their target audiences and consumer demographics. There are existing ways that mental health professionals can track professional activities related to professional, ethical, and legal responsibilities. There are many ways to purchase access to assessments and evaluations, databases, research journals, and professional mental health information. There are many ways to conduct statistical analyses on relevant professional mental health duties, tasks, and responsibilities. There are many ways that organizations can advertise products and services to mental health professionals. There are many ways to register software electronically with third parties.

I claim:

1. A method for providing an integrated user interface for one or more mental health professional, the method comprising:
   encoding a non-transitory computer readable medium with computer executable instruction, that when executed by a computer, causes the computer to perform a method, the method comprising:
      providing a user interface that provides secure electronic linkages between the software program and a plurality of remote computers; wherein the remote computers are associated with professional organizations, institutions, businesses, and/or entities associated with the one or more mental health professional;
      registering the one or more mental health professional with the professional organizations, institutions, businesses, and/or entities in order to established the secure linkages are upon; and
         wherein the one or more mental health professional includes at least one of a mental health counselor, a psychologist, a clinical social worker, a mental health clinician, a mental health researcher, a psychiatrist, a mental health student and a mental health professor; and providing a user interface that provides the one or more mental health professional data entry into a preinstalled or uploaded note template; and providing a user interface that creates and stores electronic data files including said data entry in a storage device; and providing a user interface that electronically transmits the electronic data files to the professional organizations, institutions, businesses, and/or entities;

wherein said data entry includes professional information associated with the one or more mental health professional comprising: supervision hours continuing education units, credentials, licenses, specializations, accreditations, certifications, professional memberships, professional training completed, and attendance at professional meeting or conferences; and wherein said data entry includes reimbursement information associated with the one or more mental health professional comprising: insurance board memberships with Health Maintenance organizations (HMOs), Preferred Provider Organizations (PPOs), health insurance companies, billing agencies, and third-party reimbursement entities; and wherein said data entry includes task information associated with the one or more mental health professional comprising: professional, ethical, and legal tasks, duties, and responsibilities;

providing a user interface that provides the one or more mental health professional access to mental health information;

wherein the mental health information comprises: client populations, multicultural issues, diagnostic criteria and information, formal evaluation and assessment, statistics, and ethical codes; and wherein the mental health information further comprises legal statutes, and information related to professional organizations, institutions, businesses, and/or entities, professional memberships, medications and/or psychopharmacology, consultation, and research; and wherein the mental health information pertaining to licensures, certifications, accreditations, specializations, credentials, therapeutic interventions, therapeutic theoretical orientations, educational information, and vocational information; and wherein the mental health information pertaining to continuing education opportunities, therapy notes and documentation, professional discourse and communication, developmental issues and knowledge, professional issues and knowledge, and supervision practices and regulations providing a user interface that provides the one or more mental health professional secure credit and/or monetary transactions with the professional organizations, institutions, businesses, and/or entities;

providing a user interface that provides advertising from the professional organizations, institutions, businesses, and/or entities including advertisements for products and services targeted to the one or more mental health professional.

2. The method of claim 1 further including providing a user interface that electronically transmits data files containing professional credentials associated with the one or more mental health professional to publishers and/or owners of assessments and evaluations.

3. The method of claim 1 wherein mental health information is preinstalled into the software program.

4. The method of claim 1 further including providing a user interface that electronically transmits documentation to insurance entities for reimbursement of services provided to clients associated with the one or more mental health professional.

5. The method of claim 1 further including providing an electronic fund transfer solution that processes reimbursements for mental health services rendered to clients associated with the one or more mental health professional.

6. The method of claim 1 wherein the advertising includes advertising targeted to the one or more mental health professional pertaining to professional organizations, professional conferences, professional meetings, and professional conferences.

7. The method of claim 1 wherein the advertising includes advertising targeted to the one or more mental health professional pertaining to Continuing Education Unit opportunities, hospitals, private practices, treatment centers, job postings, universities, and professional trainings, events, and memberships.

8. The method of claim 1 wherein the advertising includes advertising targeted to the one or more mental health professional pertaining to credentialing opportunities, licensing opportunities, specialization opportunities, and accreditation opportunities.

9. The method of claim 1 wherein the advertising includes advertising targeted to the one or more mental health professional pertaining to publishing companies, pharmaceutical companies, professional mental health related institutions, organizations, businesses, products, and services.

10. The method of claim 1 wherein the advertising includes advertising targeted to the one or more mental health professional pertaining to educational programs, medications, journals, databases, research, publications, books, assessments and evaluations, and other sorts of mental health related products and services.

* * * * *